United States Patent [19]

Biller

[11] Patent Number: 5,374,628

[45] Date of Patent: Dec. 20, 1994

[54] ARYL AND HETEROARYL(PHOSPHINYLMETHYL)-PHOSPHONATE SQUALENE SYNTHETASE INHIBITORS AND METHOD

[75] Inventor: Scott A. Biller, Ewing, N.J.

[73] Assignee: E. R. Squibb & Sons, Inc., Princeton, N.J.

[21] Appl. No.: 137,456

[22] Filed: Oct. 18, 1993

Related U.S. Application Data

[62] Division of Ser. No. 884,970, May 18, 1992, Pat. No. 5,278,153.

[51] Int. Cl.$^5$ .................. A61K 31/67; A61K 31/665; C07D 333/00; C07F 9/06
[52] U.S. Cl. ......................... 514/95; 514/89; 514/99; 514/107; 549/6; 549/218; 546/22; 548/413; 558/155; 558/156; 562/21
[58] Field of Search ................. 549/5, 218; 546/22; 548/413; 514/89, 95, 99

[56] References Cited

U.S. PATENT DOCUMENTS 4,871,721 10/1989 Biller ........................... 514/102

FOREIGN PATENT DOCUMENTS 0298555 1/1989 European Pat. Off. .
0356866 3/1990 European Pat. Off. .
0409181 1/1991 European Pat. Off. .

Primary Examiner—Cecilia Tsang
Attorney, Agent, or Firm—Burton Rodney

[57] ABSTRACT

Phosphonic acid squalene synthetase inhibitors are provided which are effective in lowering serum cholesterol and have the formula

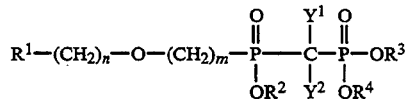

wherein m is 0 to 3, n is 1 to 5, $Y^1$ and $Y^2$ are H or halogen, $R^2$, $R^3$ and $R^4$ are H, metal ion, $C_1$ to $C_8$ alkyl, $C_3$ to $C_{12}$ alkenyl, or prodrug ester, and $R^1$ is a substituted or unsubstituted heteroaryl group or a substituted phenyl group.

18 Claims, No Drawings

ARYL AND HETEROARYL(PHOSPHINYLMETHYL)PHOSPHONATE SQUALENE SYNTHETASE INHIBITORS AND METHOD

This is a division of application Ser. No. 884,970, filed May 18, 1992, now U.S. Pat. No. 5,278,153.

FIELD OF THE INVENTION

The present invention relates to new aryl and heteroaryl(phosphinylmethyl)phosphonate compounds which are useful in inhibiting cholesterol biosynthesis by inhibiting de novo squalene production, to hypocholesterolemic and antiatherosclerotic compositions containing such compounds and to a method of using such compounds for inhibiting cholesterol biosynthesis and atherosclerosis.

BACKGROUND OF THE INVENTION

Squalene synthetase is a microsomal enzyme which catalyzes the reductive dimerization of two molecules of farnesyl pyrophosphate (FPP) in the presence of nicotinamide adenine dinucleotide phosphate (reduced form) (NADPH) to form squalene (Poulter, C. D.; Rilling, H. C., in "Biosynthesis of Isoprenoid Compounds", Vol. I, Chapter 8, pp. 413–441, J. Wiley and Sons, 1981, and references therein). This enzyme is the first committed step of the de novo cholesterol biosynthetic pathway. The selective inhibition of this step should allow the essential pathways to isopentenyl tRNA, ubiquinone, and dolichol to proceed unimpeded. Squalene synthetase along with HMG-CoA reductase have been shown to be down-regulated by receptor mediated LDL uptake (Faust, J. R.; Goldstein, J. L.; Brown, M. S. *Proc. Nat. Acad. Sci. U.S.A.* 1979, 76, 5018–5022), lending credence to the proposal that inhibiting squalene synthetase will lead to an up-regulation of LDL receptor levels, as has been demonstrated for HMG-CoA reductase, and thus ultimately should be useful for the treatment and prevention of hypercholesterolemia and atherosclerosis.

European Patent Publication 0356866A2 discloses phosphorus-containing compounds which inhibit the enzyme squalene synthetase and thus are useful as hypocholesterolemic agents and have the following structure

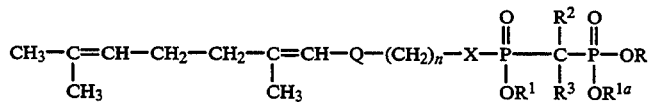

wherein Q is

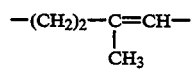

or a bond;
n is 1, 2, 3 or 4;
X is —O—, —NH—, or —NR$^4$;
R, R$^1$ and R$^{1a}$ may be the same or different and are H, lower alkyl, lower alkenyl or a metal ion;
R$^2$ and R$^3$ may be the same or different and are H or halogen;
R$^4$ is lower alkyl;

with the proviso that when x is O, n is 2, 3 or 4.

European Patent Publication 0409181A3 discloses phosphorus-containing compounds which are inhibitors of cholesterol biosynthesis (by inhibiting de novo squalene biosynthesis), and thus are useful as hypocholesterolemic agents and antiatherosclerotic agents, which have the structure

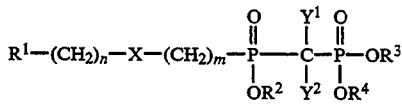

wherein m is 1, 2 or 3; n is 0, 1, 2, or 3;
Y$^1$ and Y$^2$ are H or halogen;
R$^2$, R$^3$ and R$^4$ may be the same or different and are independently H, metal ion, C$_1$ to C$_8$ alkyl or C$_3$ to C$_{12}$ alkenyl;
X is O, S, NH or NCH$_2$R$^{15}$ wherein R$^{15}$ is H or C$_1$ to C$_5$ alkyl; and
R$^1$ is R$^5$—Q$^1$—Q$^2$—Q$^3$— wherein Q$^1$, Q$^2$ and Q$^3$ are the same or different and are independently

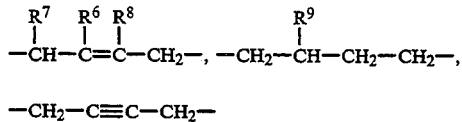

or a single bond, with the proviso that if Q$^1$ is a bond, then Q$^2$ and Q$^3$ are bonds and if Q$^2$ is a bond, then Q$^3$ is a bond, and wherein R$^6$ is H, alkyl, halo, or haloalkyl; R$^7$ is H, halo, alkyl or alkylthio; R$^8$ is H, halogen, trimethylsilyl or lower alkyl; R$^9$ is H or lower alkyl-;

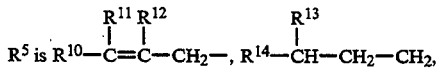

R$^{16}$—C≡C—CH$_2$— (wherein R$^{16}$ is H or lower alkyl) or CH$_3$(CH$_2$)$_p$ where p is an integer from 2 to 7; R$^{10}$, and R$^{11}$ are the same or different and are independently H, lower alkyl, halogen, haloalkyl or lower alkenyl or R$^{10}$ and R$^{11}$ can be taken together to form (CH$_2$)$_s$ where s is an integer from 2 to 7; and R$^{13}$ and R$^{14}$ are the same or different and are independently lower alkyl, with the proviso that if all of Q$^1$, Q$^2$ and Q$^3$ are bonds, then both R$^{10}$ and R$^{11}$ cannot be H and R$^5$ cannot be alkyl (CH$_2$)$_p$— with p≦4; including all stereoisomers thereof.

U.S. Pat. No. 4,871,721 to Biller et al disclose Phosphorus-containing compounds which inhibit the enzyme squalene synthetase and thus are useful as hypocholesterolemic agents and have the following structure $$CH_3-\underset{CH_3}{\underset{|}{C}}=CH-CH_2-CH_2-\underset{CH_3}{\underset{|}{C}}=CH-Q-Z-\underset{OR^1}{\overset{O}{\underset{\|}{P}}}-\underset{R^3}{\overset{R^2}{\underset{|}{C}}}-\underset{OR^{1a}}{\overset{O}{\underset{\|}{P}}}-OR$$

wherein Q is $$-(CH_2)_2-\underset{CH_3}{\underset{|}{C}}=CH-$$

or a bond;

Z is $-(CH_2)_n-$ or $-(CH_2)_p-CH=CH-(CH_2)_m-$, wherein n is 1 to 5; p is 0, 1 or 2; m is 0, 1 or 2;

R, $R^1$ and $R^{1a}$ may be the same or different and are H, lower alkyl or a metal ion; and $R^2$ and $R^3$ may be the same or different and are H or halogen.

European Pat. Publication 0298555A1 discloses bone active methylene phosphonoalkyl-phosphinic acids, and the pharmaceutically-acceptable salts and esters thereof, having the general structure $$\underset{\underset{OH}{\underset{|}{O=P-R}}}{\overset{PO_3H_2}{\overset{|}{A-C-B}}}$$

wherein the A, B, and R moieties are as defined in the EP.

DESCRIPTION OF THE INVENTION

In accordance with the present invention, there is provided phosphorus-containing compounds which inhibit cholesterol biosynthesis, and thus are useful as hypocholesterolemic and antiatherosclerotic agents and have the following structure I $$R^1-(CH_2)_n-O-(CH_2)_m-\underset{OR^2}{\overset{O}{\underset{\|}{P}}}-\underset{Y^2}{\overset{Y^1}{\underset{|}{C}}}-\underset{OR^4}{\overset{O}{\underset{\|}{P}}}-OR^3 \quad I$$

wherein m is 0, 1, 2 or 3; n is 1, 2, 3, 4 or 5; $Y^1$ and $Y^2$ are H or halogen, preferably H or F; $R^2$, $R^3$ and $R^4$ are independently H, metal ion, prodrug ester, $C_1$ to $C_8$ alkyl or $C_3$ to $C_{12}$ alkenyl; and $R^1$ is a substituted or unsubstituted heteroaryl group linked directly or indirectly to $(CH_2)_n$, or a substituted phenyl group;

$R^1$ can be defined as $R^5-Q-Y$ or $R^5-Y-Q$, wherein Y is a substituted heteroaryl group or a substituted phenyl group;

Q is an alkylene linking group, an alkenylene linking group or an alkynylene linking group or a single bond; and $R^5$ is hydrogen, an alkyl moiety, an alkenyl moiety or an alkynyl moiety.

The formula I compounds of the invention include all stereoisomers thereof as well as pharmaceutically acceptable salts thereof as indicated above as well as salts of amines and amino acids such as arginine, lysine, ammonia and the like.

Thus Q can be $$-(CH)_x-\underset{|}{\overset{R^7}{C}}=\underset{|}{\overset{R^8}{C}}-(CH_2)_t-,$$
(with $R^6$ above the double bond)

$$-(CH_2)_x-\underset{|}{\overset{R^9}{CH}}-CH_2-(CH_2)_t-,$$

$$-(CH_2)_x-C\equiv C-(CH_2)_t-,$$

$$-(CH_2)_x-\underset{\|}{\overset{}{C}}-CH_2-(CH_2)_t-,$$
(with $CH_2$ below)

or a single bond, wherein t is 0, 1, 2 or 3 and x is 0, 1, 2 or 3; $R^6$ is H, lower alkyl, halo or haloalkyl (e.g. $CH_2F$, $CF_3$); $R^7$ is H, halogen, lower alkyl or alkylthio; $R^8$ is H, halogen, trimethylsilyl or lower alkyl; $R^9$ is H, or lower alkyl;

$R^5$ can be H, $$R^{10}-\underset{|}{\overset{R^{11}}{C}}=\underset{|}{\overset{R^{12}}{C}}-(CH_2)_q-, \quad R^{14}-\underset{|}{\overset{R^{13}}{CH}}-CH_2-(CH_2)_q-,$$

$$R^{16}-C\equiv C-(CH_2)_q-$$

(wherein $R^{16}$ is lower alkyl or H), $$CH_3-\underset{\|}{\overset{}{C}}-CH_2(CH_2)_q \text{ or } CH_3(CH_2)_q-$$
(with $CH_2$ below)

where q is 0 to 5 and $R^{10}$ and $R^{11}$ are independently hydrogen, lower alkyl such as methyl or ethyl, halogen, lower alkenyl or haloalkyl or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl such as methyl or ethyl.

$R^1$ can include the following:

(phenyl ring with $R^5$, $R^{16a}$, $R^{17}$, $-Q-$ substituents), (five-membered heterocycle with $R^{16a}$, $R^{17}$, X, $Q-$ substituents), $$R^5-(CH)_x-\underset{|}{\overset{R^7}{C}}=\underset{|}{\overset{R^8}{C}}-(CH_2)_t-$$
(with $R^6$ above, attached to heterocycle with $R^{16a}$, $R^{17}$, X)

(where x is 2 or 3, the $R^7$ substituent on each carbon may be the same or different)

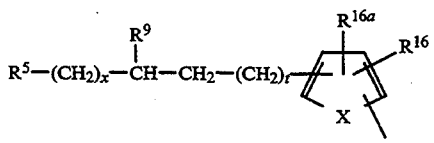

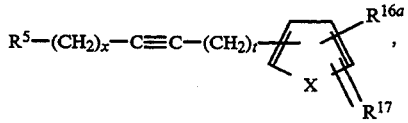

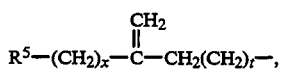

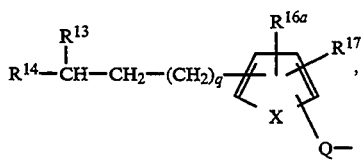

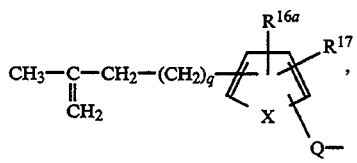

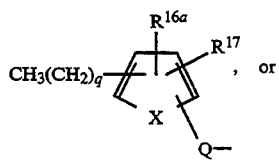

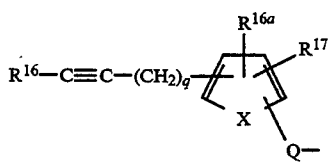

wherein X is O, S or —CH=CH—, and $R^{16a}$ and $R^{17}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino.

The terms "alkenyl" and "alkyl" as employed herein with respect to $R^1$ refer to unsubstituted alkenyl or unsubstituted alkynyl or such groups substituted with 1 to 4 groups which may be alkyl, alkenyl, alkynyl, halogen, hydroxy, alkoxy, alkenyloxy, alkynyloxy, aryl and/or cycloalkyl.

The $(CH_2)_n$, $(CH_2)_m$, $(CH_2)_x$ and $(CH_2)_t$ groups may optionally contain one or more alkyl, alkoxy, alkenyl, alkynyl, hydroxy and/or halogen substituents.

The term "prodrug esters" as employed herein includes, but is not limited to, the following groups: (1-alkanoyloxy)alkyl such as,

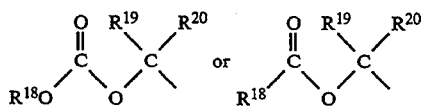

wherein $R^{18}$, $R^{19}$ and $R^{20}$ are H, alkyl, aryl or arylalkyl. Examples of such prodrug esters include $CH_3CO_2CH_2$—,

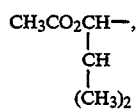

$t\text{-}C_4H_9CO_2CH_2$—, or

Other examples of suitable prodrug esters include

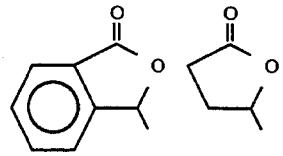

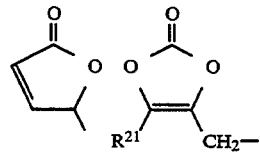

wherein $R^{21}$ is H, $CH_3$, $C_6H_5$, $t\text{-}C_4H_9$, or $R^3$ and $R^4$ can be taken together as in

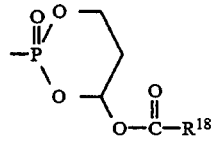

or

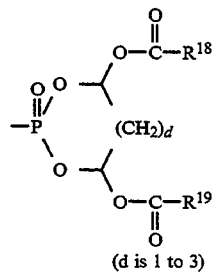

(d is 1 to 3)

Unless otherwise indicated, the term "lower alkyl" or "alkyl" as employed herein alone or as part of another group includes both straight and branched chain hydrocarbons, containing 1 to 40 carbons, preferably 1 to 20 carbons, in the normal chain, more preferably 1 to 12 carbons, such as methyl, ethyl, propyl, isopropyl, butyl, t-butyl, isobutyl, pentyl, hexyl, isohexyl, heptyl, 4,4-dimethyl pentyl, octyl, 2,2,4-trimethylpentyl, nonyl, decyl, undecyl, dodecyl, the various branched chain isomers thereof, and the like as well as such groups including 1 to 4 substituents such as F, Br, Cl or I or CF$_3$, alkoxy, aryl, arylalkyl, alkenyl, cycloalkyl, amino, hydroxy, alkylamido, alkanoylamino, arylcarbonylamino, nitro, cyano, thiol and/or alkylthio.

Unless otherwise indicated, the term "cycloalkyl" as employed herein alone or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 4 substituents such as halogen, alkyl, alkoxy, hydroxy, aryl, arylalkyl, cycloalkyl, alkylamido, alkanoylamino, arylcarbonylamino, amino, nitro, cyano, thiol and/or alkylthio.

Unless otherwise indicated, the term "aryl" or "Ar" as employed herein refers to monocyclic or bicyclic aromatic groups containing from 6 to 10 carbons in the ring portion, such as phenyl, naphthyl or phenyl or naphthyl substituted with 1 to 3 substituents such as alkyl, halogen (Cl, Br or F), alkoxy, hydroxy, amino, alkanoylamino, arylcarbonylamino, aryl, arylalkyl, cycloalkyl, alkylamido, nitro, cyano, thiol and/or alkylthio.

The term "aralkyl", "aryl-alkyl" or "aryl-lower alkyl" as used herein alone or as part of another group refers to alkyl groups as discussed above having an aryl substituent, such as benzyl or phenethyl.

The term "lower alkoxy", "alkoxy", "aryloxy" or "aralkoxy" as employed herein alone or as part of another group includes any of the above alkyl, aralkyl or aryl groups linked to an oxygen atom.

The term "lower alkylthio", "alkylthio", "arylthio" or "aralkylthio" as employed herein alone or as part of another group includes any of the above alkyl, alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 40 carbons, preferably 3 to 30 carbons in the normal chain, which include one to three double bond in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like, and which may be optionally substituted with 1 to 4 substituents, namely, halogen, alkyl, alkoxy, alkenyl, alkynyl, aryl, arylalkyl, cyclo-alkyl, amino, hydroxy, alkanoylamino, alkylamido, arylcarbonylamino, nitro, cyano, thiol and/or alkylthio.

Unless otherwise indicated, the term "lower alkynyl" or "alkynyl" as used herein by itself or as part of another group refers to straight or branched chain radicals of 2 to 40 carbons, preferably 2 to 20 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, alkyl, alkoxy, alkenyl, alkynyl, aryl, arylalkyl, cycloalkyl, amino, hydroxy, alkanoylamino, alkyl-amido, arylcarbonylamino, nitro, cyano, thiol, and/or alkylthio.

Examples of suitable $(CH_2)_t$, $(CH_2)_n$, $(CH_2)_x$ and $(CH_2)_m$ groups include

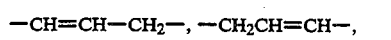

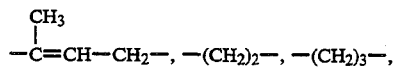

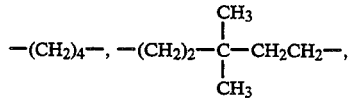

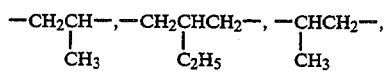

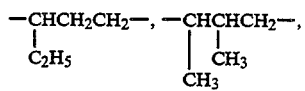

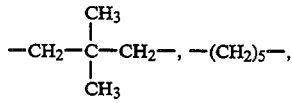

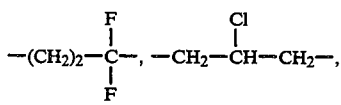

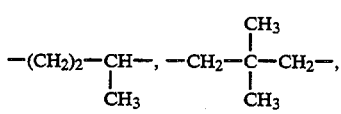

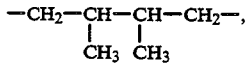

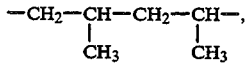

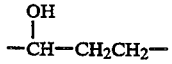

The term "halogen" or "halo" as used herein refers to chlorine, bromine, fluorine, and iodine as well as CF$_3$, with chlorine or fluorine being preferred.

The term "amino" as used herein refers to unsubstituted amino as well as monosubstituted amino or disubstituted amino wherein the substituents may be alkyl and/or aryl.

The term "metal ion" refers to alkali metal ions such as sodium, potassium or lithium and alkaline earth metal ions such as magnesium and calcium.

The term "heteroaryl" refers to furanyl, thiofuranyl, pyridinyl or pyrrolyl.

The term "haloalkyl" as used herein refers to any of the lower alkyl groups defined above substituted with a halogen as defined above, for example $CH_2F$, $CF_3$ and the like.

Preferred are those compounds of formula I which have the following formula:

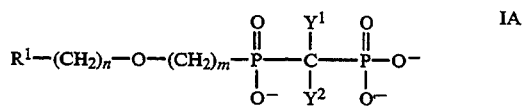

wherein m is 1 or 2; n is 1 or 2 and $R^1$ is

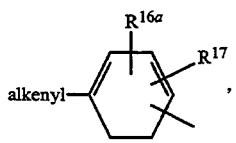

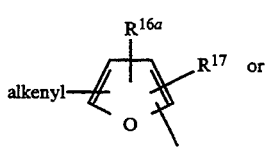 or

-continued

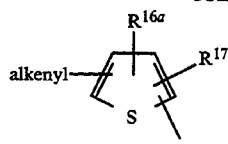

The compounds of the invention may be prepared according to the following reaction sequences.

Scheme I

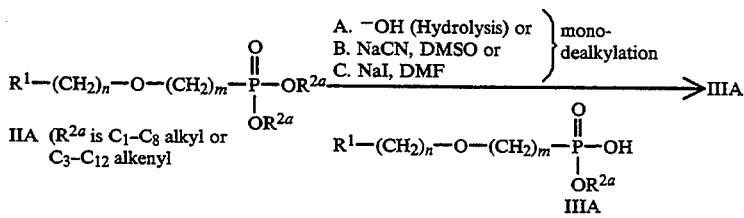

Scheme IA

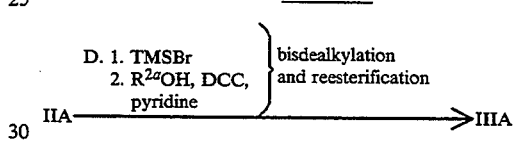

Scheme II

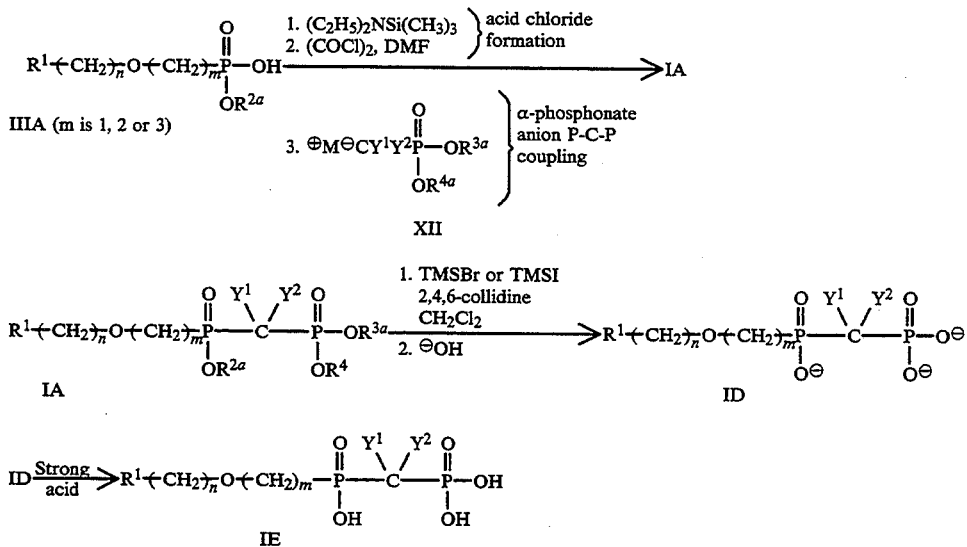

Scheme III

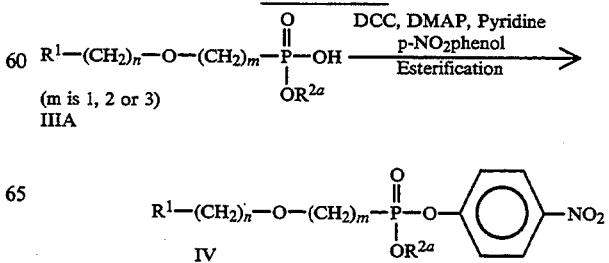

-continued
Scheme III

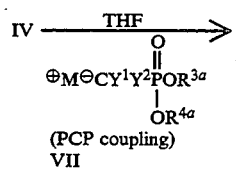
(PCP coupling)
VII

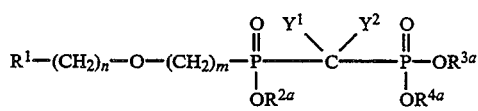

Scheme IV

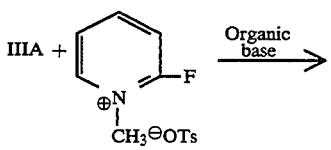

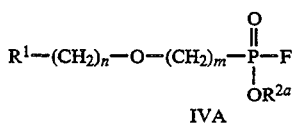
IVA

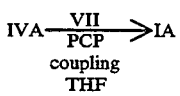
coupling
THF

Scheme V. Compounds of formula I of the invention wherein m is O, may be prepared using the methylene bisphosphonate synthesis methodology developed by Poulter, C. D. et al, *J. Org. Chem.*, 1986, 51, 4768, as outlined below:

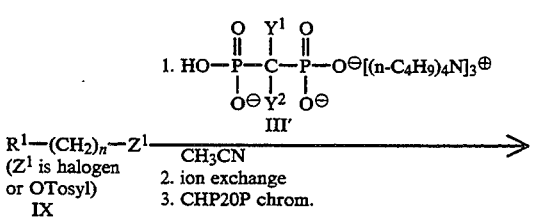

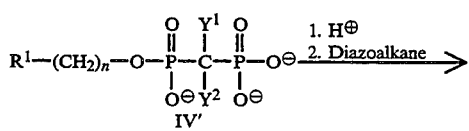

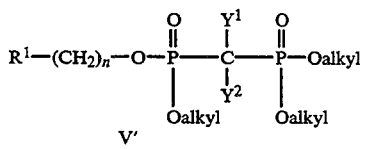

As seen in Reaction Scheme I, compounds of formula I may be prepared in accordance with the following method of the invention starting with diester IIA.

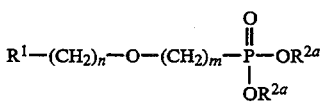

The diester IIA may be converted to the corresponding monoester IIIA

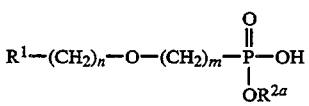

by any of four methods (A, B, C or D) as discussed below.

In Method A, diester IIA is treated with a strong aqueous base such as NaOH, KOH or LiOH, typically in the presence of a solvent such as dioxane, isopropanol, methanol or ethanol at a temperature within the range of from about 25 to about 125° C. to form monoester IIIA.

In Methods B and C of the invention, diester IIA is subjected to a monodealkylation by treatment with sodium cyanide, potassium cyanide or lithium cyanide and a solvent such as dimethyl sulfoxide or dimethylformamide (Method B) or with sodium iodide, lithium iodide or lithium chloride in the presence of a solvent such as dimethylformamide, dimethyl sulfoxide or acetone, the above reactions being carried out at a temperature of within the range of from about 40° to about 160° C., to form monoester IIIA.

In Method D of the invention (Reaction Scheme IA), diester IIa is subjected to a bisdealkylation by treating IIa with bromotrimethylsilane under an inert atmosphere such as argon in the presence of 2,4,6-collidine or triethylamine in dichloromethane and then reesterifying by reacting with an alcohol ($R^{2a}$OH) in the presence of dicyclohexylcarbodiimide (DCC) and an organic base such as pyridine, or 4-dimethylaminopyridine (DMAP) to form monoester IIIA.

As seen in Reaction Scheme II, compounds of formula I may be prepared in accordance with the following method of the invention starting with monoester IIIA which is dissolved in an inert organic solvent such as dichloromethane and treated, under an inert atmosphere such as argon, with diethyl(trimethylsilyl)amine. After evaporation of solvent, the residue is dissolved in dichloromethane or an aromatic solvent such as benzene or toluene, or other appropriate inert organic solvent, preferably containing dimethylformamide as a catalyst, under an inert atmosphere such as argon, and oxalyl chloride is added thereto. The reaction mixture is evaporated to give acid chloride V (which is a new intermediate)

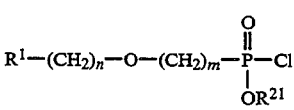

where $R^{2a}$ is $C_1$–$C_8$ alkyl or $C_3$–$C_{12}$ alkenyl.

An α-phosphonate anion P—C—P coupling is carried out on the acid chloride V as follows.

To a stirred solution of an optionally substituted dialkyl methyl phosphonate

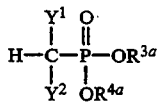

VI wherein $Y^1$, and $Y^2$ are as defined hereinbefore and $R^{3a}$ and $R^{4a}$ are independently $C_1$–$C_8$ alkyl or $C_3$–$C_{12}$ alkenyl, in an inert organic solvent such as tetrahydrofuran cooled to a temperature within the range of from about $-90°$ C. to about $0°$ C. is added a strong base, such as n-butyl lithium or lithium diisopropylamide, in hexane, tetrahydrofuran or other inert organic solvent under an inert atmosphere such as argon, followed in some instances by transmetallation by the addition of a metal halide, such as $CeCl_3$, $ZnCl_2$, $MgBr_2$, CuI, to form the metal salt VII

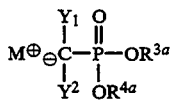

wherein M is $Li^+$, $Na^+$, $K^+$, $^+MgHal$, $^+ZnHal$, $^+Ce(Hal)_2$ or $^+Cu$ wherein Hal is a halogen ion such as $Cl^-$, $Br^-$ or $I^-$.

The metal salt VII is maintained at a reduced temperature as described above and acid chloride V in an inert organic solvent such as tetrahydrofuran or diethyl ether is added to form the phosphinyl-phosphonate IA.

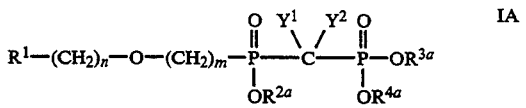

IA

The metal salt VII will be employed in a molar ratio to acid chloride V of within the range of from about 1.0:1 to about 2.5:1 and preferably from about 1.8:1 to about 2.4:1. Triester IA, in an inert organic solvent such as methylene chloride, may then be subjected to dealkylation by treating with excess bromotrimethylsilane or iodotrimethylsilane in the presence of 2,4,6-collidine or bis(trimethylsilyl)trifluoroacetamide and then treating with a strong inorganic base such as aqueous NaOH, KOH, LiOH or $Mg(OH)_2$, optionally in the presence of an alcohol such as methyl alcohol, to form the salt ID which may be separated out by chromatography. Salt ID may be treated with a strong acid such as HCl to form acid IE.

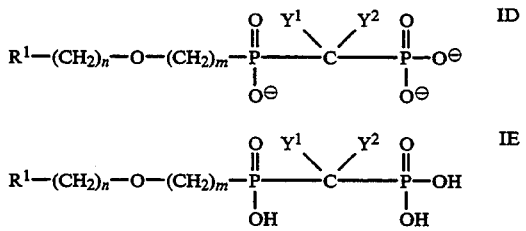

As seen in Reaction Scheme III, compounds of formula I may be prepared according to the following method of the invention starting with monoester IIIA which is dissolved in pyridine, and treated with p-nitrophenol and 4-dimethylaminopyridine and dicyclohexylcarbodiimide under an inert atmosphere such as argon at from about 25° to about 60° C. (employing a molar ratio of phenol:IIIA of within the range of from about 0.8:1 to about 1.5:1) to form the p-nitrophenyl ester IV (which is a new intermediate)

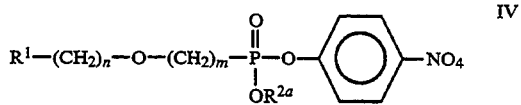

IV

An α-phosphonate anion P—C—P coupling is carried out on p-nitrophenyl ester IV by reacting nitrophenyl ester IV with metal salt VII in a manner similar to that described above to form the phosphinyl-phosphonate IA. The metal salt VII will be employed in a molar ratio to p-nitrophenyl ester IV of within the range of from about 1.0:1 to about 2.5:1 and preferably from about 1.8:1 to about 2.4:1. Triester IA may be subjected to dealkylation as described above to form ID and IE.

As seen in Reaction Scheme IV, phosphonic acid IIIa could be converted to acid fluoride IVA by treatment with 2-fluoro-1-methylpyridinium toluene-4-sulfonate and an organic base such as an amine base ($(CH_3CH_2)_3N,((CH_3)_2CH)_2NCH_2CH_3$), followed by reaction with anion VII to provide IA.

The triester IA may be hydrolyzed to the corresponding monoester IJ as follows.

Triester IA may be treated with strong inorganic bases such as KOH, NaOH or LiOH in $H_2O$ or $H_2O$/alcohol mixtures, or with nucleophiles such as, NaCN, KCN, NaI, LiCl, $NaSCH_2CH_2CH_3$ or LiBr in dimethylformamide or dimethylsulfoxide, under an inert atmosphere such as argon, employing a molar ratio of base or nucleophile to triester of within the range of from about 2:1 to about 10:1, and at a temperature within the range of from about 25° C. to about 160° C. to form the monoester IJ

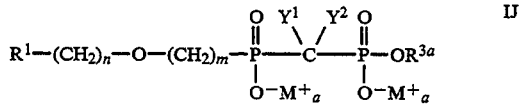

IJ where $M_a$ is an alkali metal.

As seen in the above reaction sequence V, compounds of formula V' of the invention may be prepared by treating compound IX

(where $Z^1$ is halogen of Otosyl) with dry tris(tetra-n-butyl) ammonium hydrogen diphosphonate III'

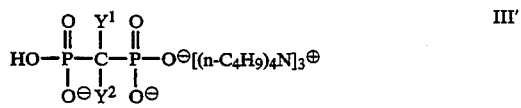

III' in an inert organic solvent such as dry acetonitrile ($CH_3CN$), tetrahydrofuran, nitromethane ($CH_3NO_2$) or methylene chloride ($CH_2Cl_2$) under an inert atmosphere such as argon, employing a molar ratio of III':IX of within the range of from about 1:1 to about 5:1 and preferably about 3:1. The solvent is removed and the residue is run through an ion exchange column to form compound IV' as an alkali metal or ammonium salt.

Compound IV' is converted to the free acid by typical acid-based extraction, and the free triacid may be treated with a diazoalkane to form the ester V. The latter reaction is carried out employing a molar ratio of diazoalkane:IV' of within the range of from about 3:1 to about >10:1 and preferably from about 3:1 to about 4:1.

The starting material IIA may be prepared in accordance with the following method starting with compound X

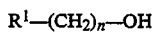

$$R^1-(CH_2)_n-OH \quad\quad X$$

which is made to undergo carbene insertion by treating a solution of x in dry deoxygenated solvent such as deoxygenated benzene under an inert atmosphere such as argon with

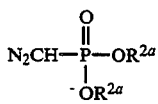

and then with phosphonate XI

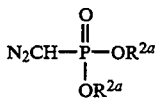

(prepared as described by Seyferth, D. et al, J.O.C. 1971, 36, 1379) in dry deoxygenated solvent as described above to form compound IIA.

In carrying out the above carbene insertion compound X is employed in a molar ratio to phosphonate XI of within the range of from about 1:1 to about 1:3 and preferably about 1:2.

The starting material IIA wherein $R^{2a}$ is alkyl and m is 1, may be prepared by reacting halide or tosylate IX

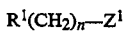

$$R^1(CH_2)_n-Z^1 \quad\quad IX$$

with phosphonate alkoxide XIa

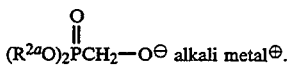

$$(R^{2a}O)_2\overset{O}{\overset{\|}{P}}CH_2-O^\ominus \text{ alkali metal}^\oplus. \quad\quad XIa$$

In another method, in accordance with the following method of the invention, starting material IIA may be prepared by alkylating X

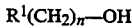

$$R^1(CH_2)_n-OH \quad\quad X$$

by treating X in an inert organic solvent such as tetrahydrofuran, diethyl ether or benzene with a base such as n-butyllithium, NaH or $((CH_3)_3-Si)_2NLi$ or a trialkylamine base such as triethyl-amine followed by treatment with XII

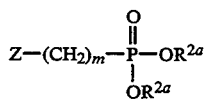

where $Z = p\text{-}CH_3C_6H_5SO_3-$, $CF_3SO_3-$ or iodide. The reaction is carried out under argon within the range of from about $-78°$ C. to about $25°$ C. to form IIa.

In carrying out the above alkylation, X will be employed in a molar ratio to phosphonate XII of within the range of from about 2:1 to about 0.5:1 and preferably from about 0.9:1 to about 1.1:1.

The phosphonate XII where m is 1 may be prepared by treating phosphite XIII

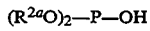

$$(R^{2a}O)_2-P-OH \quad\quad XIII$$

with paraformaldehyde and organic base such as triethylamine at a temperature within the range of from about 70° to about 120° C. under an inert atmosphere such as nitrogen to form compound XIV

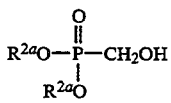

Compound XIV is dissolved in a suitable dry organic solvent such as diethyl ether, tetrahydrofuran or toluene and cooled to a temperature within the range of from about 25° C. to about $-80°$ C. and then is treated with organic base such as diisopropylethyl amine, triethyamine and pyridine, optionally containing 4-dimethylaminopyridine, and then trifluoromethanesulfonic anhydride or p-toluenesulfonyl chloride in a suitable organic solvent such as diethyl ether, dichloromethane or pyridine to form phosphonate XII where m is 1.

The above reaction is carried out employing a molar ratio of XIII: paraformaldehyde of within the range of from about 0.8:1 to about 1.2:1 and a molar ratio of XV to trifluoromethanesulfonic anhydride or tosyl chloride of within the range of from about 0.8:1 to about 1.2:1.

Phosphonate XII where m is 2 or 3 may be prepared by treating alcohol XV

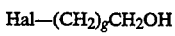

$$Hal-(CH_2)_gCH_2OH \quad\quad XV$$

where Hal is Cl, Br, or I and g is 1 or 2, with dihydropyran, employing a molar ratio of dihydropyran:XV of from about 2:1 to about 1:1, in the presence of an inert organic solvent such as methylene chloride, chloroform or toluene and catalytic amounts of p-toluenesulfonic acid or pyridinium p-toluenesulfonate at temperatures of from about 0° C. to about 25° C. to form tetrahydropyranyl ether XVI

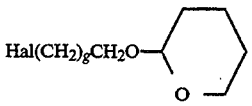

Tetrahydropyran XVI is treated with phosphite XVII

$$P(OR^{2a})_3 \quad\quad XVII$$

(in a molar ratio of XVII:XVI of from about 20:1 to about 3:1) at a temperature of from about 70 to about 160° C. to form phosphonate XVIII

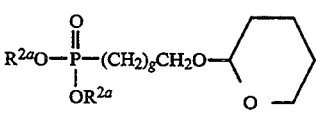

which is treated with acid such as pyridinium p-toluenesulfonate or p-toluenesulfonic acid in an alcohol solvent such as ethanol to form the phosphonate XIX

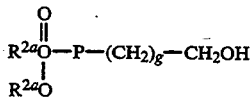

XIX

Phosphonate XIX is then treated with organic base and trifluoromethanesulfonic anhydride or p-toluenesulfonyl chloride (as described above in forming phosphonate XII where m is 1) to form phosphonate XII where m is 2 or 3.

Compound IIA where m is 2 may be prepared by a Michael addition to a vinyl phosphonate by treating a solution of compound X and tetra-n-butyl-ammonium fluoride catalyst in tetrahydrofuran or other solvent such as benzene under an inert atmosphere such as argon with a vinyl phosphonate XX (employing a molar ratio of XA:XX of from about 0.8:1 to about 1.2:1)

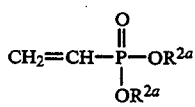

XX to form compound IIA where m is 2.

Compounds of formula IIA where m is 3 may be prepared starting with halide XXV

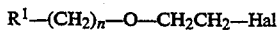

XXV where Hal is preferably Br or I, which is subjected to an α-phosphanate anion alkylation by treating XXV with phosphonate anion XXVI

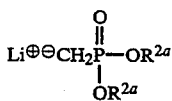

XXVI (molar ratio of XXV:XXVI of from about 1:2 to about 1:1) in an inert organic solvent such as tetrahydrofuran or diethyl ether to form compound IIA where m is 3.

Halide XXV may be prepared by treating alcohol x with sodium hydride in the presence of an inert organic solvent such as tetrahydrofuran, and the alkylating agent

in the presence of $(C_4H_9)_4NI$ followed by $(CH_3O)_2SO_2$ and the addition of a cosolvent such as dimethylformamide at from about 0° C. to about 60° C. to form ester XXVII

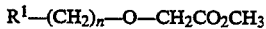

XXVII

Ester XXVII is then reduced by treating with lithium aluminum hydride, lithium triethylborohydride or lithium borohydride in the presence of diethyl ether, or tetrahydrofuran to form alcohol XXVIII

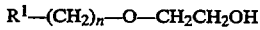

XXVIII which is then converted to the corresponding mesylate by treating XXVIII with mesyl chloride, organic base such as triethylamine in an organic solvent such as methylene chloride. The resulting mesylate is treated with a sodium halide such as sodium iodide in acetone while heating to a temperature within the range of from about 45° to about 65° C. to form halide XXV.

Halide XXVA may be converted to phosphonate IIA via an Arbuzov reaction wherein XXVA is treated with phosphite XVII

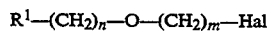

XXVA (where m =2,3)

$P(OR^{2a})_3$      XVII in a molar ratio of XVII:XXVA of from about 20:1 to about 3:1 while heating at a temperature within the range of from about 60° C. to about 160° C.

Halide XXVA where m is 2 is identical to XXV. Other examples of XXVA are made by treating X with a base, such as NaH in tetrahydrofuran at from about 0° C. to about 25° C., followed by reaction with dihalide $Hal^1$—$(CH_2)_m$—$Hal^2$, n=2,3, where $Hal^1$ and $Hal^2$ are independently Cl, Br or I.

The alcohol starting material X where n is 2, that is XB,

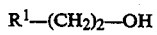

XB may be prepared according to the following reaction sequence (following the procedure of E. J. Leopold, *Organic Synthesis* 1985, 64, pp 164–173)

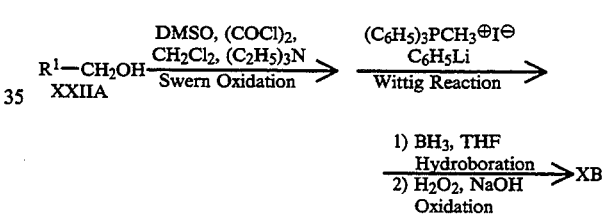

The alcohol starting material X where n is 3, that is XC,

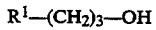

XD may be prepared according to the following reaction sequence:

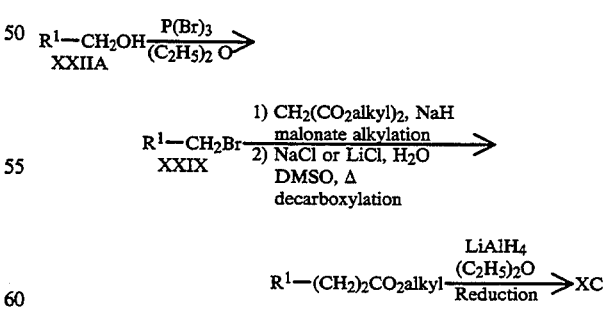

The alcohol starting material X where n is 4, that is XD

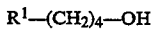

XD may be prepared according to the following reaction sequence

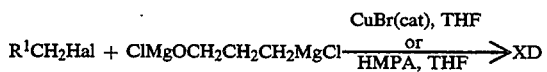

Precursors to starting material IIA having the formula XG is

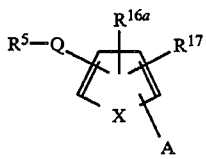

wherein X, $R^5$, $R^{16a}$ and $R^{17}$ are as defined above and A is $CH_2OR^{50}$ or $CO_2R^{51}$, and $R^{50}$ is $$CH_2\overset{O}{\underset{\|}{P}}(OR^{2a})_2 \quad \text{or} \quad -SiR_3^{60},$$

$R^{51}$ is alkyl and $R^{60}$ is alkyl or aryl (and each $R^{60}$ may be the same or different) may be prepared according to the following reaction sequence:

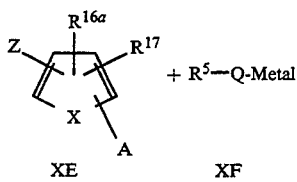

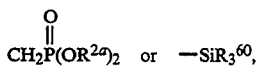

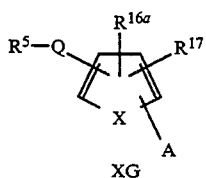

In the above compounds, Z is Cl, Br, I or $OSO_2CF_3$, A is $CH_2OR^{50}$ or $CO_2R^{51}$ and $R^{50}$ is

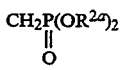

or $Si(R^{60})_3$ and $R^{51}$ is alkyl.

In compound XF Metal is MgHal, Cu, ZnHal, Sn(alkyl)$_3$, B(alkyl)$_3$, or B(OH)$_2$.

The above reaction is carried out employing a molar ratio of XF:XE of within the range of from about 2:1 to about 0.8:1, preferably from about 1.2:1 to about 1:1, in the presence of an inert organic solvent such as tetrahydrofuran, ether, dimethylformamide, or dimethyl sulfoxide, at a temperature within the range of from about $-78°$ C. to about $110°$ C., in the presence of a catalyst such as palladium or nickel catalysts.

Where XG is

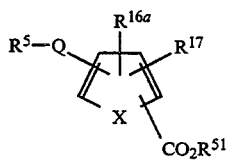

($R^{51}$ is alkyl) $XG^1$ $XG^1$ may be reduced by reaction with lithium aluminum hydride or DIBAL in the presence of ether or tetrahydrofuran at a temperature of within the range of from about $-78°$ C. to about $40°$ C., to form $XG^2$ $XG^2$

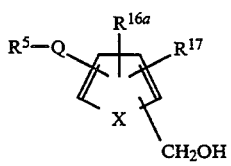

$XG^2$ may then be employed in place of X to form starting material IIA as described hereinbefore.

Where XG is

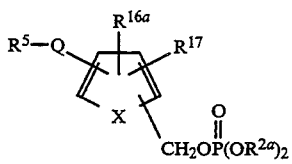

XH may be employed in place of IIA in forming compounds of the invention as described hereinbefore.

Wherein XG is

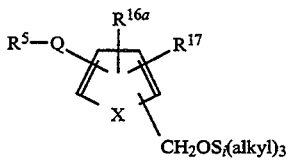

XJ may be deprotected by conventional procedures such as by treatment with fluoride to form the deprotected compound $XG^2$

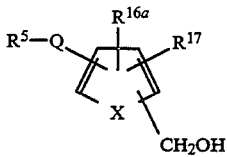

Examples of starting material X that is $R_1-(CH_2)_n-OH$ wherein n is 1, 2, 3, 4 or 5 suitable for use herein include the following which are either known in the literature or are simple derivatives of known compounds prepared by employing conventional procedures.

It will be appreciated that the compounds listed in the following table represent all possible stereoisomers.

$R^1-(CH_2)_n-OH$ where $R^1$ is $R^5QY-$ as follows in A. through F., wherein Y is

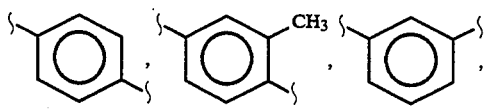
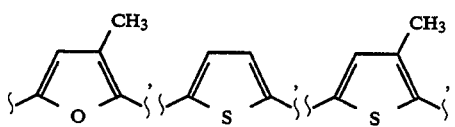
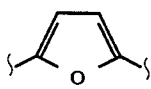
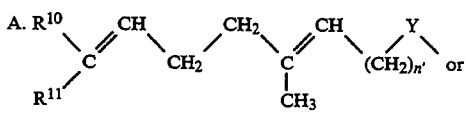
(n' is 0 to 3)
| | R¹⁰ | R¹¹ |
|---|---|---|
| 1. | $C_2H_5$ | $CH_3$ |
| 2. | $CH_3$ | $C_2H_5$ |
| 3. | $n\text{-}C_3H_7$ | $CH_3$ |
| 4. | $CH_3$ | $n\text{-}C_4H_9$ |
| 5. | $t\text{-}C_4H_9$ | $CH_3$ |
| 6. | $-(CH_2)_{s'}-$ s' = 2 to 6 | |
| 7. | H | H |
| 8. | F | F |
| 9. | Cl | Cl |
| 10. | $CH_2F$ | $CH_3$ |
| 11. | $-CH=CH_2$ | H |
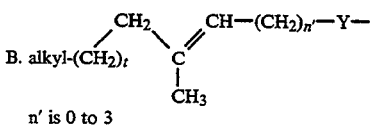
n' is 0 to 3
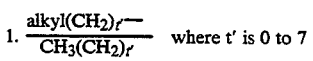
where t' is 0 to 7
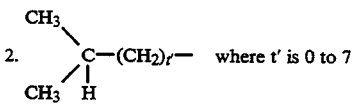
where t' is 0 to 7
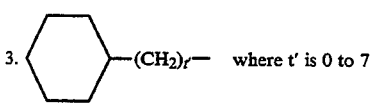
where t' is 0 to 7
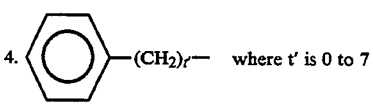
where t' is 0 to 7
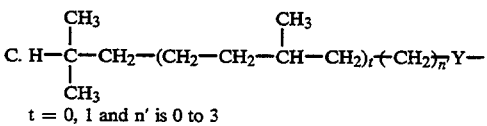
t = 0, 1 and n' is 0 to 3

-continued
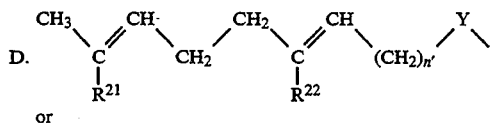
D.
or
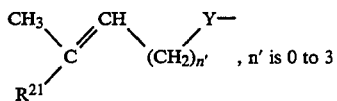
, n' is 0 to 3
| $R^{21}$ | $R^{22}$ |
|---|---|
| 1. $C_2H_5$ | $C_2H_5$ |
| 2. $C_2H_5$ | $CH_3$ |
| 3. $CH_3$ | $C_2H_5$ |
| 4. $CH_3$ | H |
| 5. H | $CH_3$ |
| 6. H | H |
E.
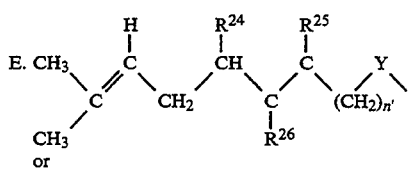
or
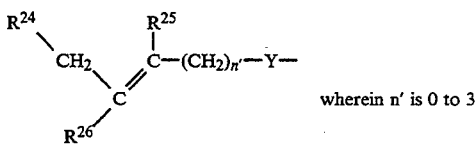
wherein n' is 0 to 3
| $R^{24}$ | $R^{25}$ | $R^{26}$ |
|---|---|---|
| 1. H | I | H |
| 2. H | H | I |
| 3. H | $CH_3$ | $CH_3$ |
| 4. $CH_3S$ | $CH_3$ | H |
| 5. F | $CH_3$ | H |
| 6. $CH_3$ | $CH_3$ | H |
| 7. H | $CH_3$ | $CH_3$ |
| 8. H | $CH_3$ | Cl |
| 9. H | $CF_3$ | H |
| 10. H | Cl | H |
| 11. H | $CH_3$ | $(CH_3)_3Si$ |
| 12. H | $CH_3$ | F |
F. Other examples of $R^1$ include the following
1. 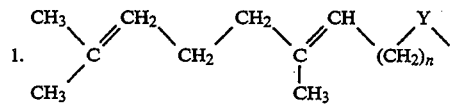
2. 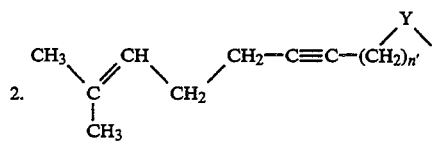
3. 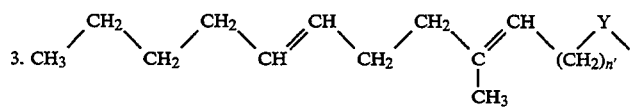
4. 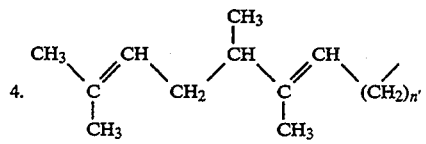

-continued
5. 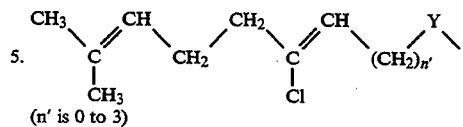
(n' is 0 to 3)
6. 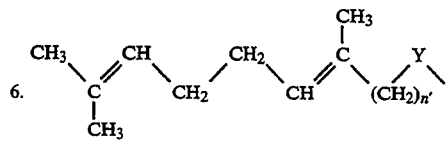
7. 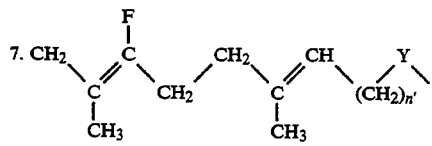
8. 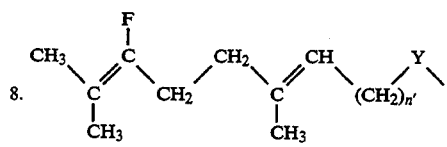
9. 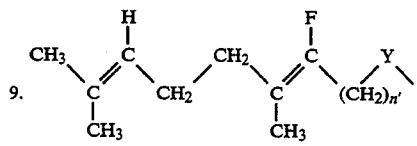
10. 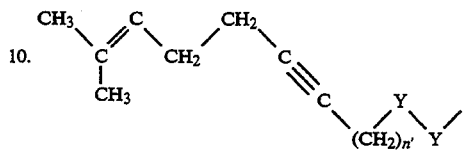
11. 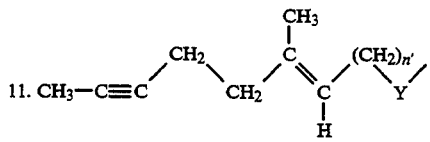
12. $CH_3-C{\equiv}C-(CH_2)_{n'}-$ (n' = 4–12)
13. $CH_3-C{\equiv}C-(CH_2)_{n'}-C{\equiv}C-CH_2)_{n2}-Y-$ (n' = 2 to 10) (n² = 0 to 3)
14. 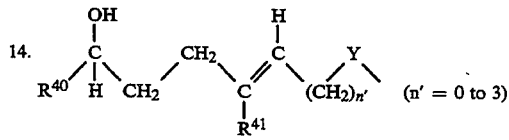 (n' = 0 to 3)
$R^{40}$=H, alkyl, cycloalkyl, or aryl such as methyl, ethyl, isopropyl, pentyl, phenyl and cyclopentyl
$R^{41}$=alkyl such as methyl, ethyl or halo such as Cl or F
15. 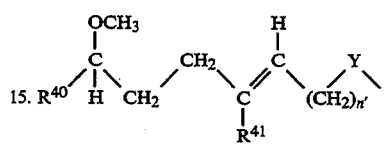
16. 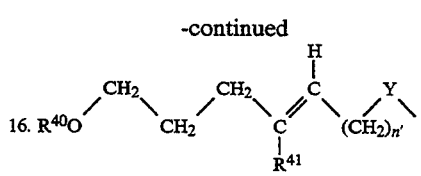
-continued
17. 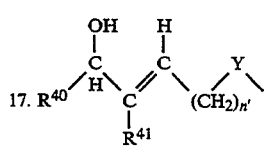

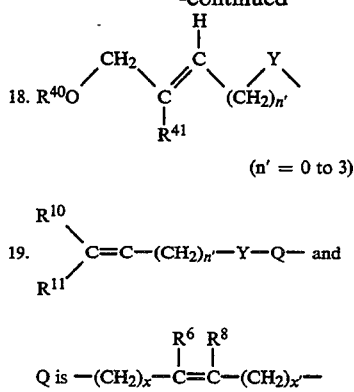

18.

(n' = 0 to 3)

19. $\overset{R^{10}}{\underset{R^{11}}{\diagdown}}C=C-(CH_2)_{n'}-Y-Q-$ and

Q is $-(CH_2)_x-\overset{R^6}{C}=\overset{R^8}{C}-(CH_2)_{x'}-$ wherein n' is 0 to 3
x is 0 to 3
x' is 0 to 3.

The compounds of Formula I of the invention inhibit cholesterol biosynthesis by inhibition of de novo squalene production. These compounds inhibit the squalene synthetase enzyme and, in addition, some of the compounds of Formula I of the invention inhibit other enzymes in the pathway from isopentenyl diphosphate to squalene, that is, farnesyl diphosphate synthetase and isopentenyl diphosphate-dimethylallyl diphosphate isomerase.

Thus, the compounds of the invention are useful in treating atherosclerosis to inhibit progression of disease and in treating hyperlipidemia to inhibit development of atherosclerosis. In addition, the compounds of the invention may increase plasma high density lipoprotein cholesterol levels.

The compounds of the invention may also be useful in inhibiting formation of gallstones, treating tumors, lowering blood pressure, lowering blood sugar, treating diabetes mellitus, treating inflammation, as a diuretic, as an inotropic agent, as an antiarthritic (antirheumatic) agent, in treating other diseases of calcium and phosphate metabolism including treatment of bone resorption, Paget's disease, osteoporosis, calcification of joints, implants and metastasis, as antitartar and anticalculus agents in toothpastes and mouthwashes, treating various stones and calculi, as well as for use in complexes with technetium-99 m and radio-iodinated derivatives for use as diagnostics.

U.S. application Ser. No. 774,957, filed Oct. 11, 1991, discloses that post-translational modification of CAAX box containing proteins may be inhibited by administering a protein-prenyl transferase inhibitor which inhibits the transfer of the prenyl group [such as farnesyl (in the case of ras oncogene products), geranyl or geranylgeranyl] to the cysteine of the CAAX box by the protein-prenyl transferase enzyme. The protein-prenyl transferase inhibitor will block the protein-prenyl transferase enzyme from catalyzing the transfer of the prenyl group (for example, farnesyl, geranyl or geranylgeranyl) from the prenyl pyrophosphate to the cys residue of the CAAX box, such as the ras p21 cys, or to the CAAX box cysteine of other CAAX box containing proteins. In the case of ras p21 oncogene products, inasmuch as the cys will not be farnesylated it cannot effect interaction of the ras protein with the membrane so that neoplastic transformation of the cell will be prevented. In this manner protein-prenyl transferase inhibitors prevent neoplastic transformation of the cell, thereby acting as an anti-cancer agent for the treatment of and/or prevention of ras-related tumors.

Examples of CAAX box containing proteins which have been demonstrated or are believed to undergo prenylation include, but are not limited to, nuclear lamins, α or γ subunits of heterotrimeric G-proteins, γ-subunits of retinal transducin, G25K and K-rev p21, and protein families including rho, rap, rac, ral, and rab.

The present invention includes a method for blocking or preventing the prenylation of CAAX box containing proteins such as ras oncogene products, and thereby inhibit disease promoting effects of the CAAX box containing protein or more specifically prevent and/or treat ras-related tumors, by administering to a patient in need of treatment a therapeutic amount of a compound of Formula I of the invention which serves as a protein-prenyl transferase inhibitor.

The Formula I protein-prenyl transferase inhibitors, unlike HMG CoA reductase inhibitors, will interfere with prenylation of the ras oncogene products and inhibit their transforming activity, yet may or may not interfere with the synthesis of FPP, a precursor in the synthesis of ubiquinones, dolichols and Haem A.

The compounds of the invention may also be employed in combination with an antihyperlipoproteinemic agent such as probucol and/or with one or more serum cholesterol lowering agents such as Lopid (gemfibrozil), bile acid sequestrants such as cholestyramine, colestipol, polidexide (DEAE-Sephadex) as well as clofibrate, nicotinic acid and its derivatives, neomycin, p-aminosalicyclic acid, bezafibrate and the like and/or one or more HMG CoA reductase inhibitors such as lovastatin, pravastatin, velostatin or simvastatin.

The above compounds to be employed in combination with the squalene synthetase inhibitor of the invention will be used in amounts as indicated in the Physicians' Desk Reference (PDR).

The compounds of the invention may also be employed with sodium lauryl sulfate of other pharmaceutically acceptable detergents to enhance oral bioavailability of such compounds.

Inhibition of squalene synthetase may be measured by the following procedure.

Rat liver microsomal squalene synthetase activity is measured using farnesyl diphosphate as substrate and quantitating squalene synthesis using gas chromatographic analysis. The assay was developed by modifying conditions originally described by Agnew (Methods in Enzymology 110: 357, 1985).

A further aspect of the present invention is a pharmaceutical composition consisting of at least one of the compounds of the invention, such as Formula I, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc., by an oral route, for example, in the form of tablets, capsules, granules or powders, or they can be administered by a parenteral route in the form of injectable preparations. The dose for adults is preferably between 200 and 2,000 mg per day, which can be administered in a single dose or in the form of individual doses from 1–4 times per day.

A typical capsule for oral administration contains active ingredient (250 mg), lactose (75 mg) and magnesium stearate (15 mg). The mixture is passed through a 60 mesh sieve and packed into a No. 1 gelatin capsule.

A typical injectable preparation is produced by asceptically placing 250 mg of sterile active ingredient into a vial, asceptically freeze-drying and sealing. For use, the contents of the vial are mixed with 2 mL of physiological saline, to produce an injectable preparation.

The following Examples represent preferred embodiments of the present invention.

Introduction to Experimental

All temperatures are reported in degrees Centigrade. $^1$H and $^{13}$C chemical shifts are reported as δ-values with respect to Me$_4$Si (δ=0). $^{31}$P spectra were measured on a JEOL FX90Q FT-NMR spectrometer, at 36.2 MHz, utilizing the $^1$H decoupled mode. The $^{31}$P data were obtained using 85% H$_3$PO$_4$ as an external reference (δ=0). Coupling constants J are reported in Hz. Chemical ionization mass spectra (CI-MS) were determined with a Finnigan TSO-4600 instrument equipped with a direct exposure probe using the indicated reagent gases. Fast atom bombardment mass spectra (FAB-MA) were recorded on a VG Analytical ZAB-2F spectrometer. Ions were sputtered (8 keV Xe) from a matrix containing dithiothreitol, dithioerythritol, DMSO, glycerol and water.

All reactions were carried out under an atmosphere of dry argon or nitrogen. The following reagents and solvents were distilled prior to use from the indicated drying agents, where applicable: CH$_2$Cl$_2$, 2,4,6-collidine, and diisopropylamine (CaH$_2$); THF and diethyl ether (K, benzophenone); N,N-diethyltrimethylsilylamine and oxalyl chloride. Benzene was passed through neutral alumina (activity I) and stored over 4A-molecular sieves. Lithium bromide was dried at 100° C. over P$_2$O$_5$.(E,E)-Farnesol was purchased from Aldrich Chemical Company.

TLC was performed on E. Merck Silica Gel 60 F-254 plates (0.25 mm) or E. Merck Cellulose F plates (0.1 mm). Flash chromatography was carried out using E. Merck Kieselgel 60 (230–400 mesh).

Reverse-phase chromatographic purification of salts or mixed ester salts was carried on CHP20P gel or SP207SS gel, highly porous, polystyrene-divinyl benzene copolymers available from Mitsubishi Chemical Industries. The indicated general procedure was followed: An FMI Model RP-SY pump was utilized for solvent delivery. A column of CHP20P or SP207SS (2.5 cm diameter, 12–22 cm height) ws slurry packed and washed with water (500–1000 mL), and a basic, aqueous solution of the crude salt was applied to the top of the column. Typically, the column was eluted with water, followed by a gradient composed of increasing concentrations of acetonitrile or methanol in water. The gradient was created by placing the tip of a tightly stoppered separatory funnel containing 300–500 mL of the organic solvent, or an aqueous-organic mixture, just beneath the surface of a reservoir containing 300–500 mL of pure water. To start the gradient, the stopcock of the separatory funnel was opened, so that as the solvent was withdrawn by the pump from the reservoir, it was replaced with the solvent from the separatory funnel. HPLC-grade solvents were employed. Fractions were collected (10–15 mL each) at a flow rate of 5–10 mL per minute. Those fractions that contained pure product as judged by TLC or HPLC were pooled, the organic solvents were evaporated and the aqueous residue was lyophilized to dryness.

EXAMPLE 1

(E)-[[[[4-(2,6-Dimethyl-1,5-heptadienyl)phenyl]methoxy]methyl](1-methylethoxy)phosphinyl]methyl]-phosphonic acid, dimethyl ester A. 6-Methyl-5-hepten-1-yne A modification of the procedure of Jacobi was followed: P. A. Jacobi, *Tetrahedron* 1987, 43, 5475–5488.

To a suspension of 12.48 g (128.8 mmol) of 95% lithium acetylide-ethylenediamine complex in 64 mL of freshly distilled dimethyl sulfoxide under argon between 5°–10° C. was added 20 g (122.6 mmol) of 5-bromo-2-methyl-2-pentene dropwise over 30 min with vigorous stirring. After the addition was complete, the mixture was allowed to warm to room temperature (RT) gradually over 1 hour (h) and then stirred at RT for 1 h. The reaction was cooled to about 15° C. and quenched by the slow addition of 25 mL of water. The reaction mixture was then distilled under reduced pressure using a short path distillation head and cooling the condenser with a 50:50 mixture of water:ethylene glycol from a circulating cold bath at −20° C. The product was collected at a boiling point range of 28°–37° C., pressure 90 mm Hg with an oil bath temp of 60°–62° C. The distillation was run under these parameters for 1 h and then the pressure was carefully lowered to 60 mm Hg and the distillation was continued for 1.5 h to provide 9.28 g of a clear, colorless oil. This material was fractionally distilled at 1 atm to provide 4.01 g (30%) of 2-methyl-2,3-pentadiene (bp 85°–90° C.), followed by 4.43 g (33%) of the title eneyne (bp 120°–125° C.) as a colorless liquid.

$^1$H-NMR (CDCl$_3$): δ5.17 (m, 1H) 2.19 (m, 4H) 1.93 (t, 1H, J=2.3 Hz) 1.70 (s, 3H) 1.62 (s, 3H) ppm.

B. (E)-1-Iodo-2,6-dimethyl-1,5-heptadiene

The following procedure of Negishi was used for the reaction: E. Negishi, *J. Am. Chem. Soc.* 1985, 107, 6639–6647.

To a stirred solution of 4.13 g (13.86 mmol) of 98% zirconocene dichloride in 35 mL of dichloromethane under argon at RT was added 13.9 mL (27.72 mmol) of 2.0M trimethyl aluminum in hexanes. The mixture was allowed to stir at RT for 0.5 h resulting in a lemon-yellow solution to which 1.5 g (13.86 mmol) of Part A eneyne was added neat and the reaction was allowed to stir at RT for 24 h. The yellow solution was cooled to −30° C. and 4.22 g (16.6 mmol) of iodine in 15 mL of tetrahydrofuran (THF) was added dropwise over 10 min. Upon addition of the iodine, the solution color turned orange-brown for a few minutes and then turned orange-yellow with precipitated solids. The mixture was allowed to warm to 0° C. and stir for 0.5 h when it was quenched with methanol and diluted with ether. The organic layer was washed with aqueous Na$_2$S$_2$O$_3$, dried over MgSO$_4$ and filtered. The solvent was removed by distillation using a fractionating column (bp 38°–40° C./1 atm) to provide a dark yellow oil as the pot residue. The remaining pot residue was further purified by bulb-to-bulb distillation (115° C./2 mm) to provide 2.32 g (67%) of title iodide as a Dale yellow oil.

$^1$H-NMR (CDCl$_3$): δ5.87 (s, 1H) 5.05 (m, 1H) 2.15 (m, 4H) 1.84 (s, 3H) 1.68 (s, 3H)
1.60 (s, 3H) ppm.

C. (E)-4-(2,6-Dimethyl-1,5-heptadienyl)benzoic acid, methyl ester

To 10 mL of THF under argon at −78° C. was added 6.1 mL (10.3 mmol) of 1.7M t-butyllithium in pentane resulting in a yellow solution, to which 1.075 g (4.29 mmol) of Part B iodide in 10 mL of THF was added dropwise over 5 min. After the addition, the reaction was allowed to stir at −78° C. for 0.5 h and then warm to 0° C. for 0.5 h. Zinc chloride (702 mg, 5.16 mmol, 1.2 equiv fuse-dried under vacuum three times) in 7 mL of THF was added via cannula to give a very pale yellow solution, which was allowed to stir at 0° C. for 1 h.

A 100 mL flask was charged 248 mg (5 mol %) of tetrakis(triphenylphosphine)palladium and 804 mg (3.07 mmol) of methyl 4-iodobenzoate in an argon filled glove bag. A volume of 10 mL of THF was added and the suspension was cooled to 0° C. when the zinc intermediate prepared above was added via cannula. The mixture was allowed to warm to RT and stir for 1.5 h when it was diluted with diethyl ether (ether) and quenched by the addition of 1N HCl solution. The organic layer was washed with water, saturated $NaHCO_3$, brine, dried over $MgSO_4$ and evaporated to provide 1.29 g of an orange-yellow oily solid. Flash chromatography was performed on 130 g of silica gel packed and loaded with 5:1 hexane/toluene and eluted with 3:1 hexane/toluene collecting 30 mL fractions. Fractions 84 to 106 were combined and evaporated to provide 602 mg (76%) of title ester in the form of a clear, colorless oil.

TLC Silica gel (9:1 hexane/ethyl acetate (EtOAc)) $R_f=0.47$. IR ($CCl_4$) 2968, 2914, 1724, 1606, 1435, 1309, 1277, 1192, 1178 $cm^{-1}$. $^1H$-NMR ($CDCl_3$): δ7.97 (d, 2H, J=8.2 Hz) 7.28 (d, 2H, J=8.2 Hz) 6.28 (s, 1H) 5.15 (m, 1H) 3.89 (s, 3H) 2.20 (m, 4H) 1.87 (d, 3H, J=1.2 Hz) 1.70 (s, 3H) 1.63 (s, 3H) ppm. MS (CI-$NH_3$, +ions) m/e 276 (M+$NH_4$), 259 (M+H).

D. (E)-4-(2,6-Dimethyl-1,5-heptadienyl)benzenemethanol

To 133 mg (3.49 mmol) of lithium aluminum hydride under argon at 0° C. suspended in 10 mL of dry ether was added 602 mg (2.32 mmol) of Part C ester in 15 mL of dry ether dropwise over 5 min. The reaction was allowed to stir at 0° C. for 0.5 h when it was quenched by the addition of 0.14 mL of water, 0.14 mL of 15% NaOH solution and then with 0.42 mL of water. After stirring for 0.5 h, $Na_2SO_4$ was added and the slurry was allowed to stir for 1 h before filtering through a pad of celite washing copiously with ether. Evaporation provided 519 mg (97%) of a pale yellow oil. The crude material was combined with 324 mg of crude product from a previous reduction on 371 mg (1.44 mmol) of Part C ester to provide 843 mg of crude produce. Flash chromatography was performed on 85 g of silica gel packed and loaded with 15:1 hexane/EtOAc and eluted with 9:1 hexane/EtOAc collecting 30 mL fractions. Fractions 34 to 85 were combined and evaporated to provide 802 mg (93%) of title alcohol as a clear, colorless oil.

TLC Silica gel (12:1 dichloromethane/EtOAc) $R_f=0.36$. IR ($CCl_4$) 3617, 3400, 2967, 2928, 2874, 2858, 1718, 1449, 1414, 1377, 1032, 1013, 795 $cm^{-1}$. $^1H$-NMR ($CDCl_3$): δ7.27 (d, 2H, J=8.2 Hz) 7.20 (d, 2H, J=8.2 Hz) 6.25 (s, 1H) 5.16 (m, 1H) 4.60 (s, 2H) 2.18 (m, 4H) 1.85 (d, 3H, J=1.2 Hz) 1.70 (s, 3H) 1.63 (s, 3H) ppm. MS (CI-$NH_3$, +ions) m/e 478 (2M+$NH_4$), 460 (2M), 248 (M+$NH_4$), 230 (M), 213 (M+H-$H_2O$). Analysis calculated for $C_{16}H_{22}O$ (M.W.=230.36): C, 83.43; H, 9.63 Found: C, 83.18; H, 9.73.

E. (E)-[[[4-(2,6-Dimethyl-1,5-heptadienyl)phenyl]methoxy]methyl]phosphonic acid, bis (1-methylethyl) ester

E(1). (Hydroxymethyl) phosphonic acid, bis (1-methylethyl) ester

A mixture of 33.2 g (0.20 mol) of diisopropyl phosphite, 2.8 mL (0.02 mol) of triethylamine, and 6.0 g (0.20 mol) of paraformaldehyde, was immersed in a 100° C. oil bath and then heated between 100°-120° C. for 45 minutes under nitrogen. An exotherm occurred within 10 minutes and all of the paraformaldehyde dissolved rapidly. The triethylamine was removed at reduced pressure, and the residue was bulb-to-bulb distilled in four portions to provide a total of 35.17 g (91%) of title compound as a colorless oil.

TLC Silica gel (5:95 $CH_3OH$: $CH_2Cl_2$) $R_f=0.17$ $^1H$ NMR ($CDCl_3$) δ4.73 (sextet, 3H, J=6 Hz) 3.84 (d, 2H, J=6 Hz), 1.34 (d, 12H, J=6 Hz) ppm. $^{13}C$ NMR ($CDCl_3$) δ70.9 (d, J=6 Hz), 57.5 (d, J=162 Hz), 23.8 (d, J=6 Hz) ppm.

E(2). [[[(Trifluoromethyl)sulfonyl]oxy]methyl]phosphonic acid, bis(1-methylethyl) ester To a stirred solution of 6.0 g (30.6 mmol) of Part A phosphonate in 100 mL of dry diethyl ether (also referred to as ether) at −78° C. was added 5.90 mL (33.9 mmol) of diisopropylethylamine followed by the addition of 5.20 mL (31.0 mmol) of trifluoromethanesulfonic anhydride in 10 mL of ether over 30 minutes. An additional 40 mL of ether was added to aid stirring through the thick precipitate. After 45 minutes at −75° C., the reaction was allowed to warm to 0° C. for 45 minutes, and the solids were filtered and washed with ether. The filtrate was evaporated to afford 9.4 g of a colorless liquid. The crude product was flash chromatographed on 150 g of silica gel eluted with 40:60 ethyl acetate:hexane to provide 5.7 g (57%) of pure title triflate as a colorless liquid.

TLC Silica gel (50:50 Ethyl Acetate:hexane) $R_f=0.34$. $^1H$ NMR ($CDCl_3$) δ4.79 (m, 2H), 4.55 (d, 2H, J=8.8 Hz), 1.37, 1.39 (two d, J=6 Hz) ppm. $^{13}C$ NMR ($CDCl_3$) δ18.5 (q, J=319 Hz), 73.0 (d, J=7.8, Hz), 67.1 (d, J=170 Hz), 23.8, 23.7 (two d, J=10 Hz) ppm.

E(3). (E)-[[[4-(2,6-Dimethyl-1,5-heptadienyl)phenyl]methoxy]methyl]phosphonic acid, bis(1-methylethyl) ester.

To a stirred solution of 773 mg (3.35 mmol) of Part D alcohol in 20 mL of THF under argon at −78° C. was added 2.2 mL (3.52 mmol) of 1.6M n-butyllithium in hexanes over 5 min. The pale yellow solution was allowed to stir at −78° C. for 40 min when 1.09 g (3.32 mmol) of the Part E(2) triflate in 5 mL of THF was added via cannula. The mixture was allowed to stir at −78° C. for 0.5 h and then warm to 0° C. After 2 h at 0° C., the reaction was quenched by the addition of saturated ammonium chloride and partitioned between ether and water. The ether layer was washed with brine, dried over $MgSO_4$ and evaporated to provide 1.53 g of a yellow oil. Flash chromatography was performed on 155 g of silica gel packed and loaded with 15:1 dichloromethane/EtOAc and eluted with 12:1

CH$_2$Cl$_2$/EtOAc collecting 50 mL fractions. Fractions 40 to 80 were combined and evaporated to provide 816 mg (60%) of title compound as a clear colorless oil.

TLC Silica gel (9:1 dichloromethane/EtOAc) R$_f$=0.21. IR (CCl$_4$) 2978, 2931, 1385, 1375, 1256, 1105, 991 cm$^{-1}$. $^1$H-NMR (CDCl$_3$) δ7.28 (d, 2H, J=8.2 Hz) 7.22 (d, 2H, J=8.2 Hz) 6.25 (s, 1H) 5.16 (m, 1H) 4.76 (m, 2H) 4.62 (s, 2H) 3.70 (d, 2H, J=8.8 Hz) 2.18 (m, 4H) 1.85 (s, 3H) 1.70 (s, 3H) 1.63 (s, 3H) 1.33 (t, 12H, J=5 Hz) ppm. MS (CI-NH$_3$, +ions) m/e 426 (M+NH$_4$), 409 (M+H).

F. (E)-[[[4-(2,6-Dimethyl-1,5-heptadienyl)phenyl]methoxy]methyl]phosphonic acid, mono (1-methylethyl) ester To a stirred solution of 790 mg (1.93 mmol) of Part E compound in 10 mL of 2-propanol under argon was added 9.9 mL (9.90 mmol) of 1M potassium hydroxide and the mixture was heated to 100° C. for 33 h. The 2-propanol solvent was evaporated and the aqueous residue was stirred in dichloromethane and acidified by the addition of 10% HCl solution. The organic layer was washed with water, brine, dried over MgSO$_4$ and evaporated to provide 692 mg (98%) of title compound as a pale yellow oil.

TLC Silica gel (8:1:1 n-C$_3$H$_7$OH/con. NH$_3$/H$_2$O) R$_f$=0.50.

G. (E)-[[[[4-(2,6-Dimethyl-1,5-heptadienyl)phenyl]methoxy]methyl](1-methylethoxy)phosphinyl]methyl]phosphonic acid, dimethyl ester To a stirred solution of 692 mg (1.89 mmol) of Part F compound in 7 mL of dichloromethane under argon at RT was added 0.72 mL (3.78 mmol) of N,N-diethyltrimethylsilylamine and the reaction was allowed to stir at RT for 1.5 h. The solvent was evaporated and the residue was dissolved in benzene, evaporated and pumped at high vacuum. The remainder was dissolved in 8 mL of dichloromethane containing 3 drops of dimethyl formamide (DMF) under nitrogen at 0° C. and 1.89 mL (3.78 mmol) of 2M oxalyl chloride in dichloromethane was added dropwise over 10 min with much gas evolution. After 45 min at 0° C., the reaction was allowed to stir at RT for 45 min. The solvent was evaporated and the residue was dissolved in benzene, evaporated and pumped at high vacuum for 1 hour.

To a solution of 0.45 mL (4.16 mmol) of dimethyl methylphosphonate in 6 mL of THF under argon at −78° C. was added 2.5 mL (3.97 mmol) of 1.6M n-butyllithium in hexanes over 10 min to give a white suspension. After 40 min at −78° C., the acid chloride prepared above was added in 10 mL of THF over 10 min. The reaction was allowed to stir at −78° C. for 1 h when it was quenched by the addition of saturated ammonium chloride and diluted with ether. The aqueous layer was made acidic with 10% HCl and the ether layer was separated and washed with brine. The aqueous layer was re-extracted with dichloromethane and the dichloromethane layer was washed with brine. The combined organic layers were dried over MgSO$_4$ and evaporated to provide 870 mg of crude product. Flash chromatography was performed on 90 g of silica gel eluted with 2:98 methanol/dichloromethane collecting 50 mL fractions. Fractions 40 to 72 were combined and evaporated to provide 621 mg (70%) of title compound as a clear, colorless oil.

TLC Silica gel (5:95 methanol/dichloromethane) R$_f$=0.23. IR (CCl$_4$) 2978, 2955, 2930, 2855, 1256, 1231, 1063, 1036, 993, 841 cm$^{-1}$. $^1$H-NMR (CDCl$_3$): δ7.28 (d, 2H, J=8.8 Hz) 7.21 (d, 2H, J=8.2 Hz) 6.25 (s, 1H) 5.15 (m, 1H) 4.76 (m, 1H) 4.65 (d, 1H, J=12 Hz) 4.58 (d, 1H, J=12 Hz) 3.88–3.76 (m, 2H) 3.81, 3.76 (two d, 6H total, J=11 Hz) 2.50 (m, 2H) 2.18 (m, 4H) 1.86 (s, 3H) 1.70 (s, 3H) 1.63 (s, 3H) 1.35, 1.31 (two d, 6H total, J=5 Hz) ppm. MS (CI-NH$_3$, +ions) m/e 490 (M+NH$_4$), 473 (M+H).

EXAMPLE 2

(E)-[[[[4-(2,6-Dimethyl-1,5-heptadienyl)phenyl]methoxy]methyl]hydroxyphosphinyl]methyl]phosphonic acid, trisodium salt To a stirred solution of 614 mg (1.29 mmol) of Example 1 product in 8 mL of dichloromethane under argon at RT was added 0.50 mL (3.89 mmol) of 2,4,6-collidine followed by 1.0 mL (7.79 mmol) of bromotrimethylsilane and the reaction was allowed to stir at RT for 18 h. The solvent was evaporated and pumped at high vacuum for 1 h. The remainder was dissolved in 7.8 mL (7.8 mmol) of 1M NaOH, stirred for 1 hour, diluted with water and lyophilized. The crude material was purified by MPLC on a column of CHP20P (2.5 cm diameter×23 cm height) eluted with water (fraction 1 to 14) followed by a gradient created by the gradual addition of 500 mL of acetonitrile to a reservoir of 450 mL of water. Approximately 8 mL fractions were collected and the pH at fraction 14 was about pH=10. Fractions 35 to 42 were combined, the acetonitrile was removed at reduced pressure and the aqueous solution was lyophilized to provide 348 mg (57%) of an amorphous white lyophilate which was >98% pure by HPLC. Fractions 43 to 45 were combined, the acetonitrile was removed at reduced pressure and the aqueous solution was lyophilized to provide 191 mg (31%) of title salt as an amorphous white lyophilate which was >95% pure by HPLC.

TLC Silica gel (5:4:1 n-C$_3$H$_7$OH/con. NH$_3$/H$_2$O) R$_f$=0.37. IR (KBr) 3437, 2969, 2856, 1645, 1377, 1107, 1082, 1055, 970, 866, 800, 765,708 cm$^{-1}$. $^1$H-NMR (D$_2$O): δ7.38 (d, 2H, J=8.1 Hz) 7.28 (d, 2H, J=8.1 Hz) 6.28 (s, 1H) 5.20 m, 1H) 4.61 (s, 2H) 3.70 (d, 2H, J=6.2 Hz) 2.18 (m, 4H) 1.94 (t, 2H, J=18 Hz) 1.83 (s, 3H) 1.64 (s, 3H) 1.59 (s, 3H) ppm. MS (FAB, +ions) m/e 469 (M+H), 447 (M+2H-Na), 423 (M+3H-2Na). Analysis Calculated for C$_{18}$H$_{25}$Na$_3$O$_6$P$_2$.1.5 H$_2$O (Effective MW=495.37): C, 43.65; H, 5.70; P, 12.51 Found: C, 43.77; H, 5.63; P, 12.65.

EXAMPLE 3

(E)-[[[[4-(2,6-Dimethyl-1,5-heptadienyl)-2-methylphenyl]methoxy]methyl](1-methylethoxy)phosphinyl]methyl]phos-phonic acid, dimethyl ester Compounds A to E were prepared according to the procedure of O. Sato: Bull. Chem. Soc. Japan, 1957, 30, 508–513.

A. N-(4-Acetyl-3-methylphenyl)acetamide

The reaction was run in a 500 mL 3 neck round bottom (RB) fitted with a mechanical stirrer and reflux condenser. To 45 g (301.6 mmol) of 3-methylacetanilide in 240 mL of carbon disulfide under argon at RT was added 38.6 mL (542.8 mmol) of acetyl chloride with stirring. To the solution was then added 145 g (1.09 mol) of aluminum chloride in small portions over a 1 h period. After addition was complete the mixture was refluxed for 1 h and then allowed to cool and stand for 1 h. The supernatant carbon disulfide layer was decanted off and the very dark viscous lower layer was poured into a mixture of cracked ice and hydrochloric acid. The precipitate was collected and washed with 1 L of water. The solid was dried under high vacuum for 30 h at RT no provide 52.17 g (90%) of title amide in the form of a light tan solid which is used as the crude material in the following reaction.

B. 1-(4-Amino-2-methylphenyl)-1-ethanone

A mixture of 52.17 g (273.0 mmol) of Part A amide in 500 mL of 2M HCl was heated to reflux for 25 h and after cooling was basified with aqueous sodium hydroxide. The organic material was extracted with ether and the ether extract was dried over potassium carbonate. The solvent was evaporated to provide 37.5 g (92%) of a light brown solid. The crude material was dissolved with heating in 100 mL of toluene, gravity filtered and allowed to cool slowly. The solid was collected after 4 hours and washed with 100 mL of a 1:1 mixture of hexane/toluene. The solid was dried under high vacuum at RT for 17 h to provide 27.2 g (67%) of title amine as a light brown solid. mp 92°–94° C. (lit mp 94°–95° C.).

C. 1-(4-Iodo-2-methylphenyl)-1-ethanone

To 5 g (33.5 mmol) of Part B amine in 20 mL of water was added 3.9 mL (70.3 mmol) of 98% $H_2SO_4$ in 100 mL of water with slight heating to give a pale yellow solution. The mixture was cooled to 0° C. and a few pieces of ice were added. The sodium nitrite (2.3 g, 33.5 mmol) in 10 mL of $H_2O$ was added slowly over 10 min to give a darker yellow solution. Upon addition of the sodium nitrite the flask was gently swirled and ice chunks were added as the first ones melted.

Potassium iodide 8.3 g (50.3 mmol) was dissolved in 15 mL of water and the solution was cooled to 0° C. The diazonium salt prepared above was cautiously poured into an addition funnel and added dropwise over a 30 min period. Upon addition of the diazonium salt, the clear potassium iodide solution turned orange-brown in color. After the addition was complete the mixture was allowed to stir at 0° C. for 40 min, then gradually warm to RT followed by 60° C. for 2 h. After heating, two phases were present. There was a very dark organic layer and a light yellow aqueous layer. The mixture was extracted with ether and the ether layer was washed with 1M NaOH, aqueous sodium thiosulfate, water, brine, dried over $MgSO_4$ and evaporated to provide 8.35 g (96%) of a very dark brown oil. The crude material was bulb-to-bulb distilled (145° C., 1.7 mm) to provide 4.3 g (49%) of title iodide as an orange-brown oil.

D. 4-Iodo-2-methylbenzoic acid

To a stirred solution of 6.6 g (165.1 mmol) of sodium hydroxide in 100 mL of water at −10° C. was added 2.45 mL (47.6 mmol) of bromine to give a yellow solution to which 3.3 g (12.7 mmol) of Part C iodide in 20 mL of dioxane was added dropwise over 1 h. After addition the mixture was allowed to stir between −10° C. to 0° C. for 1 h and then warmed to 50° C. for 1 h. The excess sodium hypobromite was decomposed by the addition of sodium sulfite. Upon addition of the sodium sulfite the solution color turned from yellow to very pale yellow. The solution was concentrated to about ½ volume on the rotovapor to remove the bromoform. The remaining aqueous solution was acidified with 10% HCl to give a white precipitate. The precipitate was collected and washed with water. The solid was recrystallized from ethanol/water to provide 2.35 g (71%) of title acid as a white solid after drying under high vacuum at RT for 50 h.

E. 4-Iodo-2-methylbenzoic acid, methyl ester

To a stirred solution of 2.35 g (8.96 mmol) of Part D acid in 25 mL of methanol was added 0.11 mL (2.06 mmol) of 98% $H_2SO_4$ and the reaction was heated to reflux for 18 h. The solution volume was concentrated to about 15 mL and diluted with 100 mL of ether. The ether layer was washed with water, saturated $NaHCO_3$, brine, dried over $MgSO_4$ and evaporated to provide 2.3 g of a pale yellow oil. Flash chromatography was performed on 230 g of silica gel packed and loaded with 12:1 hexane/EtOAc and eluted with 10:1 hexane/EtOAc collecting about 30 mL fractions. Fractions 18 to 25 were combined and evaporated to provide 2.01 g (81%) of title iodide as a clear colorless oil.

TLC Silica gel (3:1 hexane/EtOAc) $R_f$=0.73 $^1$H NMR ($CDCl_3$, 270MHz) δ7.60 (m, 2H) 7.59 (s, 1H) 3.87 (s, 3H) 2.54 (s, 3H) ppm.

F. (E)-4-(2,6-Dimethyl-1,5-heptadienyl)-2-methylbenzoic acid, methyl ester

To 35 mL of THF under argon at −78° C. was added 14.4 mL (24.4 mmol) of 1.7M t-butyllithium in pentane resulting in a yellow solution to which 2.55 g (10.2 mmol) of the Example 1 Part B vinyl iodide in 15 mL of THF was added dropwise over 10 min. After the addition, the reaction was allowed to stir at −78° C. for 0.5 h and then warmed to 0° C. for 0.5 h. Zinc chloride (1.67 g, 12.2 mmol), (fuse-dried under vacuum three times), in 30 mL THF was added via cannula to give a very pale yellow solution, which was allowed to stir at 0° C. for 1 h.

A 100 mL RB flask was charged with 421 mg (5 mol %) of tetrakis (triphenylphosphine) palladium (0) and 2.01 g (7.28 mmol) of Part E iodide in an argon filled glove bag. A volume of 15 mL of THF was added and the suspension was cooled to 0° C. when the zinc intermediate prepared above was added via cannula. The mixture was allowed to warm to RT and stir for 1 h when it was diluted with ether and quenched by the addition of 1N HCl solution. The organic layer was washed with water, saturated $NaHCO_3$, brine, dried over $MgSO_4$ and evaporated to provide 2.14 g of an orange-brown oil with solids present. Flash chromatography was performed on 215 g of silica gel packed and loaded with 5:1 hexane/toluene and eluted with 3:1 hexane/toluene collecting 30 mL fractions. Fractions 61 to 128 were combined and evaporated to provide 1.47 g (74%) of title ester as a clear colorless oil.

TLC Silica gel (9:1 hexane/Ethyl acetate) $R_f$=0.41 IR ($CCl_4$) 3019, 2968, 2928, 2855, 1722, 1604, 1444, 1434, 1380, 1260,1190, 1151, 1084 cm$^{-1}$ $^1$NMR (270 MHz) δ7.87 (d, 1H, J=8.2 Hz) 7.10 (d, 1H, J =8.2 Hz) 7.08 (s, 1H) 6.23 (s, 1H) 5.15 (m, 1H) 3.86 (s, 3H) 2.59 (s, 3H) 2.19 (m, 4H) 1.87 (d, 3H, J =0.8 Hz) 1.70 (s, 3H) 1.63 (s, 3H) ppm. MS (CI, +ions) m/e 290 (M+$NH_4$), 273 (M+H). Anal. Calcd. for $C_{18}H_{24}O_2$: C, 79.37 ; H, 8.88. Found: C, 79.48; H, 9.05.

G.
(E)-4-(2,6-Dimethyl-1,5-heptadienyl)-2-methylbenzenemethanol

To 167 mg (4.40 mmol) of lithium aluminum hydride under argon at 0° C. was added 15 ml of dry ether, and 800 mg (2.94 mmol) of Part F ester in 20 ml of dry ether was added dropwise over 5 min. The reaction was allowed to stir at 0° C. for 0.5 h when it was quenched by the addition of 0.18 ml of $H_2O$, 0.18 ml of 15% NaOH solution and then with 0.53 ml of $H_2O$. After stirring for 0.5 h, $Na_2SO_4$ was added and the slurry was stirred for 1 h before filtering through a pad of Celite washing copiously with ether. Evaporation provided 708 mg of a clear colorless oil as the crude product. Flash chromatography was performed on 75 g of silica gel packed and loaded with 12:1 hexane/ethyl acetate and eluted with 9:1 hexane/ethyl acetate collecting 30 ml fractions. Fractions 54 to 87 were combined and evaporated to provide 638 mg (89%) of title alcohol as a clear colorless oil.

TLC Silica gel (6:1 hexane/ethyl acetate) $R_f=0.23$ IR (CCl$_4$) 3617, 3300, 2967, 2917, 2882, 2856, 1657, 1609, 1499, 1447, 1406, 1376, 1211, 1179, 1106, 1037, 893, 831 cm$^{-1}$ 1H NMR (270MHz) $\delta$7.26 (d, 1H, J=7.6 Hz) 7.05 (d, 1H, J=7.6 Hz) 7.04 (s, 1H) 6.22 (s, 1H) 5.16 (m, 1H) 4.62 (s, 2H) 2.33 (s, 3H) 2.18 (m, 4H) 1.85 (s, 3H) 1.70 (s, 3H) 1.63 (s, 3H) ppm. MS (CI, +ions) m/e 262 (M+NH$_4$), 244 (M), 227 (M+H-H$_2$O). Anal. Calcd. for C$_{17}$H$_{24}$O: C, 83.55 ; H, 9.90 Found: C, 83.31; H, 10.08

H.
(E)-[[[4-(2,6-Dimethyl-1,5-heptadienyl)-2-methylphenyl]methoxy]methyl]phosphonic acid, bis(1-methylethyl) ester To a stirred solution of 620 mg (2.54 mmol) of Part G alcohol in 15ml of THF under argon at −78° C. was added 1.67 ml (2.67 mmol) of 1.6M n-butyllithium in hexanes over 10 min. The reaction was allowed to stir for 40 min. at −78° C. when 825 mg (2.51 mmol) of the Example 1 Part E(2) triflate in 15 ml of THF was added via cannula. The reaction was allowed to stir for 40 min. at −78° C. and then allowed to warm of 0° C. After 2h at 0° C. the reaction was quenched by the addition of saturated NH$_4$Cl and partitioned between ether and water. The ether layer was washed with brine, dried over MgSO$_4$ and evaporated to provide 1.26 g of a pale yellow oil as the crude product. Flash chromatography was performed on 130 g of silica gel packed and loaded with 10:1 hexane/acetone and eluted with 7:1 hexane/acetone collecting 50 ml fractions. Fractions 53 to 78 were combined and evaporated to provide 694 mg (65%) of a clear colorless oil. The 694 mg was rechromatographed on 70 g of silica gel packed and loaded with 5:1 hexane/EtOAc and eluted with 3:1 hexane/EtOAc collecting 30 ml fractions. Fractions 63 to 97 were combined and evaporated to provide 682 mg (64%) of title compound as a clear colorless oil.

TLC Silica gel (9:1 dichloromethane/EtOAc) $R_f=0.16$ 1H NMR (270MHz) $\delta$7.24 (d, 1H, J=8.8 Hz) 7.05 (m, 2H) 6.22 (s, 1H) 5.15 (m, 1H) 4.76 (m, 2H) 4.63 (s, 2H) 3.71 (d, 2H, J=8.2 Hz) 2.34 (s, 3H) 2.18 (m, 4H) 1.86 (s, 3H) 1.64 (s, 3H) 1.33 (t, 12H, J=6 Hz) ppm.

I.
(E)-[[[4-(2,6-Dimethyl-1,5-heptadienyl)-2-methylphenyl]methoxy]methyl]phosphonic acid, mono(1-methylethyl) ester.

To a stirred solution of 682 mg (1.61 mmol) of Part H compound in 10 ml of 2-propanol under argon was added 8.2 ml (8.20 mmol) of 1M KOH solution and the reaction was heated to 100° C. for 16 h. The 2-propanol was evaporated and the aqueous residue was stirred in dichloromethane and acidified with 10% HCl. The organic layer was washed with water, brine, dried over MgSO$_4$ and evaporated to provide 603 mg (98%) of title compound as a clear colorless oil.

TLC Silica gel (8:1:1 n-C$_3$H$_7$OH/con.NH$_3$/H$_2$O) $R_f=0.47$

J.
(E)-[[[[[4-(2,6-Dimethyl-1,5-heptadienyl)-2-methylphenyl]methoxy]methyl](1-methylethoxy)phosphinyl]methyl]phosphonic acid, dimethyl ester To a stirred solution of 603 mg (1.58 mmol) of Part I compound in 7 ml of dichloromethane under argon at RT was added 0.61 ml (3.17 mmol) of N,N-diethyltrimethylsilylamine and the reaction was allowed to stir at RT for 1.5 h. The solvent was evaporated and the residue was dissolved in benzene, evaporated, and pumped at high vacuum for 0.5 hour. The remainder was dissolved in 10 ml of dichloromethane containing 3 drops of DMF under nitrogen at 0° C. and 1.58 ml (3.17 mmol) of 2M oxalyl chloride in dichloromethane was added dropwise over 10 min with much gas evolution. After 45 min. at 0° C. the reaction was allowed to warm to RT for 45 min. The solvent was evaporated and the residue was dissolved in benzene, evaporated, and pumped at high vacuum for 1 h.

To a solution of 0.38 ml (3.48 mmol) of dimethyl methylphosphonate in 7 ml of THF under argon at −78° C. was added 2.1 ml (3.32 mmol) of 1.6M n-butyllithium in hexanes over 10 min to give a white suspension. After 40 min at −78° C. the acid chloride prepared above was added in 10ml of THF over 10 min. and the reaction was allowed to stir at −78° C. for 1 h when it was quenched with saturated NH$_4$Cl solution and diluted with ether. The aqueous layer was made acidic with 10% HCl solution and the organic layer was separated and washed with brine. The aqueous layer was reextracted with dichloromethane and the dichloromethane layer was separated and washed with brine. The combined organic layers were dried over MgSO$_4$ and evaporated to provide 837 mg of yellow oil as the crude product. Flash chromatography was performed on 100 g of silica gel packed, loaded, and eluted with 2:98 methanol/dichloromethane collecting 50 ml fractions. Fractions 32 to 54 were combined and evaporated to provide 327 mg (42%) of title compound as title compound as a clear colorless oil.

TLC Silica gel (5:95 Methanol/dichloromethane) $R_f=0.27$ IR (CCl$_4$) 2976, 2926, 2876, 2854, 1450, 1384, 1375, 1255, 1178, 1165, 1089, 1035, 991 cm$^{-1}$. 1H NMR (270 MHz) $\delta$7.22 (d, 1H, J=8.2 Hz) 7.05 (m, 2H) 6.22 (s, 1H, H$_6$) 5.16 (m, 1H) 4.77 (m, 1H) 4.66 (d, 1H, J=12 Hz) 4.58 (d, 1H, J=12 Hz) 3.90 (dd, 1H, J=13.5, 5.8 Hz) 3.80, 3.76 (two d, 6H total, J=11 Hz) 3.8-3.7 (m, 1H) 2.49 (m, 2H) 2.34 (s, 3H) 2.18 (m, 4H) 1.86 (s, 3H) 1.70 (s, 3H) 1.63 (s, 3H) 1.35, 1.30 (two d, 6H total, J=6 Hz) ppm. MS (CI, +ions) m/e 504 (M+NH$_4$), 487

(M+H). Anal. Calcd. for $C_{24}H_{40}O_6$ $P_2$: C, 59.25; H, 8.29 Found: C, 58.81; H, 8.49

EXAMPLE 4

(E)-[[[[[4-(2,6-Dimethyl-1,5-heptadienyl)-2-methylphenyl]methoxy]methyl]hydroxyphosphinyl]methyl]-phosphonic acid, trisodium salt To a stirred solution of 302 mg (0.621 mmol) of Example 3 product in 7 ml of dichloromethane under argon at RT was added 0.30 ml (1.86 mmol) of 2,4,6-collidine followed by 0.50 ml (3.73 mmol) of bromo-trimethylsilane and the reaction was allowed to stir at RT for 20 h. The solvent was evaporated and pumped at high vacuum for 1 h. The remainder was dissolved in 3.7 ml (3.70 mmol) of 1M NaOH solution, stirred for 1 h, diluted with water and lyophilized. The crude material was purified by MPLC on a column of CHP20P (2.5 cm diameter×20 cm height) eluted with water fractions (1 to 14) followed by a gradient created by the gradual addition of 500 ml of acetonitrile to a reservoir of 450 ml of water. Approximately 12 ml fractions were collected and the pH at fraction 14 was about pH=10. Fractions 34 to 38 were combined and the acetonitrile was evaporated at reduced pressure and the aqueous solution was lyophilized to provide 187 mg (62%) of title salt as an amorphous white lyophilate.

TLC Silica gel (5:4:1 n-$C_3H_7OH$/con. $NH_3/H_2O$) $R_f$=0.37 IR (KBr) 3426, 2965, 2922, 2870, 1639, 1448, 1381, 1180, 1151, 1092, 1051, 968, 698 $cm^{-1}$. 1H NMR ($D_2O$) $\delta$7.33 (d, 1H, J=8.2 Hz) 7.10 (m, 2H) 6.23 (s, 1H) 5.18 (m, 1H) 4.65 (s, 2H) 3.70 (d, 2H, J=5.9 Hz) 2.29 (s, 3H) 2.15 (m, 4H) 1.94 (t, 2H, J=18 Hz) 1.81 (s, 3H) 1.63 (s, 3H) 1.57 (s, 3H) ppm. MS (FAB, +ions) m/e 505 (M+Na), 483 (M+H). Anal. Calcd. for $C_{19}H_{27}Na_3O_6P_2 \cdot 1.55$ $H_2O$: C, 44.72; H, 5.95; P, 12.14 Found: C, 44.72; H, 5.65; P, 11.91

EXAMPLE 5

(E)-[[[[[5-(2,6-Dimethyl-1,5-heptadienyl)-3-methyl-2-furanyl]methoxy]methyl](1-methylethoxy)phosphinyl]-methyl]phosphonic acid, dimethyl ester

A. 3-(2,2-Dimethoxyethyl)-3-methyloxiranecarboxylic acid, methyl ester

Reference: D. M. Burness *Org Syn* 1959, 39, 49.

A 1L 3-neck RB flask fitted with a mechanical stirrer, thermometer and powder addition funnel was charged with 65.5 mL (0.492 mol) of 4,4-dimethoxy-2-butanone and 69 mL (0.787 mol) of methyl chloroacetate and 400 mL of dry ether under an argon atmosphere. The mixture was cooled to −10° C. and 42.5 g (0.787 mol) of sodium methoxide was added slowly over 2 h making sure that the temperature did not go above −5° C. Upon addition of the sodium methoxide the solution color turned pale yellow and after addition was complete the color was a bright yellow. The mixture was allowed to stir at −10° C. for 2 h and then gradually warm to RT and stir overnight. The orange-yellow solution was cooled to 0° C. and made acidic by the addition of 5 mL of acetic acid in 75 mL of water. The ether layer was separated and washed with water, saturated $NaHCO_3$, brine, dried over $MgSO_4$ and evaporated under vacuum to provide 117 g of the crude title glycidic ester as an orange-brown oil which was used directly in the next step.

B. 3-Methyl-2-furancarboxylic acid, methyl ester

Reference: D. M. Burness *Org Syn* 1959, 39, 49.

The crude Part A glycidic ester was fractionally distilled under argon at 1 atm keeping the pot temperature around 160° C. The heating was continued until the distillation of methanol (bp 59°–66° C.) essentially ceases or the theoretical amount (31.5 g, 40 mL) collected. After the oil bath cooled the remaining pot residue was distilled under reduced pressure using the same fractionating column. The distillation was done at 8 mm-Hg, bp 70°–75° C. with an oil bath temperature of 90°–115° C. to provide 44.87 g (65%) of title compound as a clear colorless oil which solidified in the receiver flask. Literature bp 72°–78° C./8 mm-Hg 1H NMR ($CDCl_3$) $\delta$7.44 (d, 1H, J=1.76 HZ) 6.36 (d, 1H, J=1.76 HZ) 3.89 (S, 3 H, $OCH_3$) 2.36 (S, 3 H, $CH_3$) ppm.

C. 3-Methyl-2-furancarboxylic acid

Reference: D. M. Burness *Org Syn* 1959, 39, 628.

A stirred mixture of 10 g (7.13 mmol) of Part B compound in 25 mL of 20% NaOH solution was heated to reflux for 2 h. The reaction was allowed to cool to RT and acidified with 15 mL of concentrated HCl. The reaction was stirred for 10 min to ensure freeing of the acid from its salt form, then cooled to RT before the white precipitate is collected by suction filtration and washed with 20 mL of water. The solid was taken up into ether and washed with water, brine, dried over $MgSO_4$ and evaporated. The white solid was taken up into 15 mL of ether with some slight heating and then diluted with about 15 mL of hexane. The solution was warmed to drive off about ½ of the ether and then allowed to cool slowly. Crystals started to form after a few minutes and when the flask cooled to RT it was placed in the refrigerator for about 1 h. The solid was collected and washed with 10 mL of cold hexane and then pumped at high vacuum for about 20 h to provide 6.35 g (71%) of title acid as a white solid. mp 133°–135° C., Literature mp 134°–135° C. 1H NMR ($CDCl_3$) $\delta$12.6 (s, 1H, $CO_2H$) 7.51 (d, 1H, J=1.76 Hz) 6.40 (d, 1H, J=1.76 Hz) 2.40 (s, 3 H, $CH_3$) ppm.

D. 5-Iodo-3-methyl-2-furancarboxylic acid

See: D. W. Knight *JCS Perking I*, 1981, 1125.

To a stirred solution of 16.2 mL (115.4 mmol) of freshly distilled diisopropylamine in 170 mL of THF under argon at −78° C. was added 61 mL (97.7 mmol) of 1.6M n-butyllithium (n-BuLi) in hexanes to give a pale yellow solution. The reaction was allowed to stir at −78° C. for 15 min and then warm to 0° C. After 0.5 h at 0° C. the solution was cooled again to −78° C. 5 and 5.6 g (44.4 mmol) of Part C acid in 110 mL of THF was added dropwise over 10 min to give a dark yellow solution. The reaction was allowed to stir at −78° C. for 1 h when 24.8 g (97.7 mmol) of iodine in 60 mL of THF was added over 10 min to give a dark solution. The reaction was allowed to stir at −78° C. for 1 h when it was diluted with ether and acidified with 10% HCl solution. The ether layer was washed with water, saturated $NaHSO_3$, brine, dried over $MgSO_4$ and evaporated to provide 12.5 g of title iodide as a brown-yellow solid which was used as the crude in the following reaction. 1H NMR ($CDCl_3$) $\delta$6.58 (s, 1H) 2.35 (s, 3 H, $CH_3$) ppm.

E. 5-Iodo-3-methyl-2-furancarboxylic acid, methyl ester

A solution of 11.2 g (44.4 mmol) of Part D iodide in 140 mL of DMF under argon at RT was added 12.3 g (88.8 mmol) of $K_2CO_3$ followed by 13.8 mL (222.2 mmol) of methyl iodide and the reaction was allowed to stir overnight. The reaction was diluted with ether and made acidic by the addition of 10% HCl solution. The organic layer was washed with water, brine, dried over $MgSO_4$ and evaporated to provide 12 g of a tan solid. Flash chromatography was performed on 1200 g of silica gel packed and loaded with 2:1 hexane/$CH_2Cl_2$ and eluted with 1:1 hexane/$CH_2Cl_2$ collecting 50 mL fractions. Fractions 28 to 89 were combined and evaporated to provide 8.87 g (75%) of title ester as a white solid. mp 83°–86° C.

TLC Silica gel (1:1 hexane/$CH_2Cl_2$) $R_f=0.29$ IR (KBr) 3437, 3117, 2951, 1709, 1601, 1464, 1393, 1292, 1153, 1105 cm$^{-1}$. $^1$H NMR (CDCl$_3$) δ6.53 (s, 1H) 3.88 (s, 3H) 2.32 (s, 3H) ppm. MS (CI, +ions) m/e 284 (M+NH$_4$), 267 (M+H). $^{13}$C NMR (CDCl$_3$)

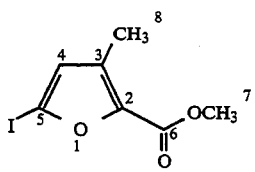

158.6 (C$_6$), 145.5 (C$_2$), 133.3 (C$_3$), 125.6 (C$_4$), 93.9 (C$_5$), 51.6 (C$_7$), 11.1 (C$_8$) ppm.

F. (E)-5-(2,6-Dimethyl-1,5-heptadienyl)-3-methyl-2-furancarboxylic acid, methyl ester To 20 mL of THF under argon at −78° C. was added 9.7 mL (16.4 mmol) of 1.7M t-butyllithium in pentane to give a yellow solution to which 1.71 g (6.85 mmol) of Example 1 Part B vinyl iodide in 10 mL of THF was added dropwise over 10 min. The reaction was stirred at −78° C. for 0.5 h and then allowed to warm to 0° C. and stir for 0.5 h. zinc chloride (1.12 g, 8.22 mmol, fuse-dried under vacuum three times), in 30 mL of THF was added via syringe to give a very pale yellow solution which was allowed to stir at 0° C. for 1 h.

A 100 mL flask was charged with 282 mg (5 mol %) of tetrakis(triphenylphosphine)palladium and 1.3 g (4.89 mmol) of methyl 5-iodo-3-methyl-2-furoate (Part E) in an argon filled glove bag. A volume of 20 mL of THF was added and the mixture was cooled to 0° C. The zinc intermediate prepared above was then added via cannula and the reaction was allowed to stir at 0° C. for 1 h and then warm to RT and stir for 1 h when it was diluted with ether and quenched by the addition of 1N HCl. The ether layer was washed with water, saturated NaHCO$_3$, brine, dried over MgSO$_4$ and evaporated to provide 1.93 g of an orange-brown oil with solids present. Flash chromatography was performed on 200 g of silica gel packed and loaded with 2:1 hexane/toluene and eluted with 1:1 hexane/toluene collecting 50 mL fractions. Fractions 32 to 86 were combined and evaporated to provide 1.09 g (85%) of title compound as a pale yellow oil.

TLC Silica gel (9:1 hexane/EtOAc) $R_f=0.42$. IR (CCl$_4$) 2963, 2926, 2856, 1709, 1599, 1438, 1376, 1299, 1101 cm$^{-1}$. $^1$H NMR (CDCl$_3$) δ6.16 (s, 1H) 6.10 (s, 1H) 5.10 (m, 1H) 3.87 (s, 3H) 2.33 (s, 3H) 2.18 (m, 4H) 2.00 (d, 3H, J=1.18 Hz) 1.68 (s, 3H) 1.61 (s, 3H) ppm. MS (CI, +ions) m/e 280 (M+NH$_4$), 263 (M+H). Anal. calcd. for C$_{16}$H$_{22}$O: C, 73.25 ; H, 8.45 Found: C, 72.67; H, 8.63

G. (E)-5-(2,6-Dimethyl-1,5-heptadienyl)-3-methyl-2-furanmethanol

To 216 mg (5.70 mmol) of lithium aluminum hydride under argon at 0° C. was added 20 mL of dry ether and 997 mg (3.80 mmol) of Part F compound in 25 mL of dry ether was added dropwise over 5 min. After 10 min at 0° C., the reaction was quenched by the addition of 0.2 mL of H$_2$O, 0.2 mL of 15% NaOH and then with 0.7 mL of H$_2$O. After stirring for 0.5 h, NaSO$_4$ was added and the slurry was stirred for 1 h before filtering through a pad of celite, washing copiously with ether. Evaporation provided 902 mg of a pale yellow oil. Flash chromatography was performed on 90 g of silica gel packed and loaded with 10:1 hexane/EtOAc and eluted with 9:1 hexane/EtOAc collecting 50 mL fractions. Fractions 59 to 82 were combined and evaporated to provide 839 mg (94%) of title alcohol as a pale yellow oil.

TLC Silica gel (4:1 hexane/EtOAc) $R_f=0.23$. IR (CCl$_4$) 3335, 2967, 2925, 2859, 1658, 1445, 1377 cm$^{-1}$. $^1$H NMR (CDCl$_3$,) δ6.01 (s, 2H) 5.11 (m, 1H) 4.53 (s, 2H) 2.15 (m, 4H) 2.02 (s, 3H) 1.95 (s, 3H) 1.68 (s, 3H) 1.61 (s, 3H) ppm. MS (CI, +ions) m/e 235 (M+H), 217 (M+H-H$_2$O). Anal. calcd. for C$_{15}$H$_{22}$O$_2$: C, 76.88; H, 9.46 Found: C, 76.95; H, 9.94

H. (E)-[[[5-(2,6-Dimethyl-1,5-heptadienyl)-3-methyl-2-furanyl]methoxy]methyl]phosphonic acid, bis(1-methylethyl)ester To a stirred solution of 1.09 g (4.67 mmol) of Part G alcohol in 25 mL of THF under argon at −78° C. was added 5.1 mL (5.14 mmol) of 1M lithium bis(trimethylsilyl)amide in THF dropwise over 5 min. The reaction was allowed to stir at −78° C. for 20 min when 1.53 g (4.67 mmol) of the Example 1 Part E(2) triflate in 20 mL of THF was added via cannula. The reaction was allowed to stir at −78° C. for 0.5 h and then warm to 0° C. and stir for 2 h when it was quenched with saturated NH$_4$Cl and partitioned between ether and water. The ether layer was washed with water, brine, dried over MgSO$_4$ and evaporated to provide 1.81 g of a yellow oil. Flash chromatography was performed on 180 g of silica gel packed and loaded with 4:1 hexane/EtOAc and eluted with 2:1 hexane/EtOAc collecting 50 mL fractions. Fractions 39 to 72 were combined and evaporated to provide 1.14 g (59%) of title compound as a pale yellow oil.

TLC Silica gel (1:1 hexane/EtOAc) $R_f=0.24$. IR (CCl$_4$) 2978, 2929, 2879, 1450, 1376, 1257, 1106, 992 cm$^{-1}$. $^1$H NMR (270MHz) δ6.02 (s, 1H) 5.99 (s, 1H) 4.75 (m, 2H) 4.54 (s, 2H) 3.70 (d, 2H, J=8.8 Hz) 2.16 (m, 4H) 2.04 (s, 3H) 1.95 (s, 3H) 1.68 (s, 3H) 1.61 (s, 3H) 1.32 (t, 12H total, J=5.9 Hz) ppm. MS (CI, +ions) m/e 430 (M+NH$_4$), 412 (M). Anal. calcd. for C$_{22}$H$_{37}$O$_5$P.0.55 H$_2$O: C, 62.55; H, 9.09; P, 7.33 Found: C, 62.54; H, 9.02; P, 7.23

I.
(E)-[[[5-(2,6-Dimethyl-1,5-heptadienyl)-3-methyl-2-furanyl]methoxy]methyl]phosphonic acid, mono(1-methylethyl) ester To a stirred solution of 500 mg (1.21 mmol) of Part H compound in 10 mL of 2-propanol was added 6.2 mL (6.20 mmol) of 1M KOH and the reaction was heated to 90° C. for 20 h. The 2-propanol was evaporated and the aqueous residue was stirred in $CH_2Cl_2$ and acidified with 1M $KHSO_4$ solution. The organic layer was washed with water, brine, dried over $MgSO_4$ and 10 eq (0.97 mL) of pyridine was added before evaporation which provided 840 mg of title compound as a yellow oil as the pyridinium salt.

TLC Silica gel (8:1:1 n-$C_3H_7OH$/con $NH_3/H_2O$) $R_f=0.46$.

J.
(E)-[[[5-(2,6-Dimethyl-1,5-heptadienyl)-3-methyl-2-furanyl]methoxy]methyl]phosphonic acid, 1-methylethyl 4-nitrophenyl ester To a stirred solution of 544 mg (1.21 mmol) of Part I compound in 6 mL of pyridine was added 185 mg (1.33 mmol) of p-nitrophenol, 15 mg of 4-dimethylaminopyridine (DMAP) and finally 374 mg (1.81 mmol) of dicyclohexylcarbodiimide (DCC) in 6 mL of pyridine. The reaction was warmed to 50° C. and stirred overnight under an argon atmosphere. Another 0.5 eq (84 mg) of p-nitrophenol and 0.5 eq (125 mg) of DCC were added and the reaction was allowed to stir for 5 h at 50° C. The pyridine was evaporated and the residue was dissolved in $Et_2O$) to precipitate dicyclohexyl urea (DCU). The DCU was filtered and the solvent evaporated. Flash chromatography was performed on 100 g of CC7 silica gel packed and loaded with 5:1 hexane/EtOAc and eluted with 3:1 hexane/EtOAc collecting 15 mL fractions. Fractions 18 to 42 were combined and evaporated to provide 490 mg of a yellow oil which proved by proton NMR to be a 1:1 mixture of p-nitrophenol to the desired title p-nitrophenol ester.

TLC Silica gel (5:95MeOH/$CH_2Cl_2$) $R_f=0.81$.

K.
(E)-[[[[5-(2,6-Dimethyl-1,5-heptadienyl)-3-methyl-2-furanyl]methoxy]methyl](1-methylethoxy)phosphinyl]methyl]phosphonic acid, dimethyl ester To a stirred solution of 0.29 mL (2.72 mmol) of dimethyl methylphosphonate in 5 mL of THF under argon at −78° C. was added 1.65 mL (2.64 mmol) of 1.6M n-BuLi in hexanes over 5 min to give a white suspension. The mixture was allowed to stir for 40 min when 490 mg (0.777 mmol) of Part J p-nitrophenol ester in 10 mL of THF was added dropwise over 5 min to give a yellow solution. The reaction was allowed to stir at −78° C. for 1 h when it was diluted with ether and quenched with saturated $NH_4Cl$. The aqueous layer was made acidic by the addition of 1M $KHSO_4$. The organic layer was separated and washed with water and brine. The aqueous layer was reextracted with $CH_2Cl_2$ and the organic layer was washed with water and brine. The combined organic layers were dried over $MgSO_4$ and evaporated to provide 557 mg of a dark yellow oil. Flash chromatography was performed on 60 g of silica gel packed and loaded and eluted with 2.98MeOH/$CH_2Cl_2$ collecting 30 mL fractions. Fractions 67 through 94 were combined and evaporated to provide 214 mg (37% overall yield from Part H compound) of title compound as a pale yellow oil.

TLC Silica gel (5:95 $CH_3OH/CH_2Cl_2$) $R_f=0.21$. IR ($CCl_4$) 2961, 2926, 2856, 1623, 1449, 1376, 1254, 1033, 993, 816 cm$^{-1}$. $^1H$ NMR ($CDCl_3$) δ6.03 (s, 1H) 5.99 (s, 1H) 5.12 (m, 1H) 4.75 (m, 1H) 4.55 (d, 1H, J=12 Hz) 4.50 (d, 1H, J=12 Hz) 3.86–3.76 (m, 2H) 3.81, 3.76 (two d, 6H total, J=11 Hz) 2.52 (m, 2H) 2.16 (m, 4H) 2.05 (s, 3H) 1.95 (s, 3H) 1.69 (s, 3H) 1.62 (s, 3H) 1.35, 1.29 (two d, 6H total, J=6.45 Hz) ppm.

EXAMPLE 6
(E)-[[[[[5-(2,6-Dimethyl-1,5-heptadienyl)-3-methyl-2-furanyl]methoxy]methyl]hydroxyphosphinyl]methyl]phosphonic acid, trisodium salt To a stirred solution of 210 mg (0.441 mmol) of Example 5 product in 4 mL of dichloromethane under argon at RT was added 0.17 mL (1.32 mmol) of 2,4,6-collidine followed by 0.35 mL (2.65 mmol) of bromotrimethylsilane and the reaction was allowed to stir at RT for 25 h. The solvent was evaporated and pumped at high vacuum for 1 h. The remainder was dissolved in 2.6 mL (2.60 mmol) of 1M NaOH, stirred for 1 h, diluted with water and lyophilized. The crude material was purified by MPLC on a column of CHP-20P (2.5 cm diameter×21 cm height) eluted with water fractions (1 to 15) followed by a gradient created by the gradual addition of 500 mL of 70:30 $CH_3CN/H_2O$ to a reservoir of 450 mL of water. Approximately 10 mL fractions were collected and the pH at fraction 15 was pH=10. Fractions 36 to 39 were combined, the acetonitrile was evaporated at reduced pressure and the aqueous solution was lyophilized to provide 126 mg (60%) of title salt as an amorphous white lyophilate which was >95% pure by HPLC.

TLC Silica gel (5:4:1 n-$C_3H_7OH$/con $NH_3/H_2O$) $R_f=0.35$. IR (KBr) 3442, 2968, 2925, 1698, 1633, 1379, 1178, 1088, 1050, 970 cm$^{-1}$. $UV1_{max}$ (Diode Array Detector)=278 nM $^1H$ NMR (400 MHz, $D_2O$) δ6.19 (s, 1H) 6.03 (s, 1H) 5.15 (m, 1H) 4.52 (s, 2H) 3.66 (d, 2H, J=6.4 Hz) 2.16 (br s, 4 H) 1.98 (s, 3H) 1.93 (t, 2H, J=18 Hz) 1.90 (s, 3H) 1.63 (s, 3H) 1.57 (s, 3H) ppm. MS (FAB, +ions) m/e 473 (M+H), 451 (M+2H-Na). Anal. calcd. for $C_{17}H_{25}Na_3P_2O_7 \cdot 1.24 H_2O$: C, 41.29; H, 5.60; P, 12.53 Found: C, 41.25; H, 5.34; P, 12.18

EXAMPLE 7
(E)-[[[[[5-(2,6-Dimethyl-1,5-heptadienyl)-2-thienyl]methoxy]methyl](1-methylethoxy)phosphinyl]methyl]phosphonic acid, dimethyl ester

A.
(E)-5-(2,6-Dimethyl-1,5-heptadienyl)-2-thiophenecarboxylic acid, methyl ester A(1). 5-Iodo-2-thiophenecarboxylic acid To a stirred solution of 10.9 mL (78.0 mmol) of freshly distilled diisopropylamine in 150 mL of THF under argon at −78° C. was added 48.7 mL (78.0 mmol) of 1.6M n-BuLi in hexanes to give a pale yellow solution which was allowed to stir at −78° C. for 10 min when 5.0 g (39.0 mmol) of 2-thiophenecarboxylic acid in 31 mL of THF was added dropwise over 10 min to give a grey-white suspension. The metallation was allowed to proceed for 30 min when 8.77 g (39.0 mmol) of N-iodosuccinimide in 25 mL of THF was added very rapidly to give an orange-yellow solution which was allowed to gradually warm to 0° C. After 0.5 h at 0° C., the brown-yellow mixture was quenched with water, diluted with ether and made acidic by the addition of solid citric acid to give a very dark brown-orange solution. The organic layer was separated and washed with water, saturated NaHSO$_3$, brine, dried over MgSO$_4$ and evaporated to provide 9.5 g (96%) of title acid as a brown-yellow solid which was used directly in the following reaction.

A(2). 5-Iodo-2-thiophenecarboxylic acid, methyl ester

To a stirred solution of 9.5 g (37.4 mmol) of Part A(1) acid in 100 mL of DMF was added 10.3 g (74.8 mmol) of K$_2$CO$_3$ followed by 11.6 mL (186.9 mmol) of methyl iodide and the reaction was allowed to stir under argon at RT overnight. The reaction was diluted with ether and acidified with 1N HCl solution. The organic layer was separated and washed with water, brine, dried over MgSO$_4$ and evaporated to provide 9.2 g of solid. The crude material was recrystallized from hexane to provide 7.86 g (79%) of title ester as a light brown solid. mp 90°-91° C., lit mp 88°-90° C. [Gronowitz, S.; Arkin För Keni Vol. 21 (1963)].

TLC Silica gel (3:1 hexane/EtOAc) R$_f$=0.53. IR (KBr) 3078, 2950, 1712, 1695, 1527, 1265, 752 cm$^{-1}$. $^1$H NMR (CDCl$_3$) δ7.42 (d, 1H, J=3.5 Hz) 7.25 (d, 1H, J=4 Hz) 3.87 (s, 3 H, OCH$_3$ ) ppm. MS (CI-NH$_3$, +ions) m/e 286 (M+NH$_4$), 268 (M). Anal. calcd. for C$_6$H$_5$IO$_2$S: C, 26.88; H, 1.88; I, 47.34; S, 11.96 Found: C, 26.52; H, 2.09; I, 47.05; S, 11.65

A(3). (E)-5-(2,6-Dimethyl-1,5-heptadienyl)-2-thiophenecarboxylic acid, methyl ester To 20 mL of THF under argon at −78° C. was added 11.0 mL (18.8 mmol) of 1.7M t-butyllithium in pentane to give a yellow solution to which 1.96 g (7.83 mmol) of Example 1 Part B vinyl iodide in 10 mL of THF was added dropwise over 5 min. After addition the reaction was allowed to stir at −78° C. for 0.5 h and then warm to 0° C. and stir for 0.5 h. Zinc chloride (1.28 g, 9.40 mmol) (fuse-dried under vacuum three times) in 25 mL of THF was added via syringe to give a very pale yellow solution which was allowed to stir at 0° C. for 1 h.

A 250 mL RB flask was charged with 323 mg (5 mol %) of tetrakis(triphenylphosphine)palladium and 1.5 g (5.59 mmol) of methyl 5-iodo-2-thiophenecarboxylate in an argon filled glove bag. A volume of 30 mL of THF was added and the suspension was cooled to 0° C. when the zinc intermediate prepared above was added via cannula. The reaction was allowed to warm to RT and stir for 1 h when it was diluted with ether and quenched by the addition of 1N HCl solution. The ether layer was separated and washed with water, saturated NaHCO$_3$, brine, dried over MgSO$_4$ and evaporated to provide 2.03 g of an orange-yellow oil with solids present. Flash chromatography was performed on 200 g of silica gel packed and loaded with 3:1 hexane/toluene and eluted with 1:1 hexane/toluene collecting about 50 mL fractions. Fractions 22 to 41 were combined and evaporated to provide 1.15 g (78%) of title compound as a clear colorless oil.

TLC Silica gel (3:1 hexane/EtOAc) R$_f$=0.60. IR (CCl$_4$) 2965, 2925, 2855, 1713, 1524, 1447, 1288, 1261, 1097 cm$^{-1}$. $^1$H NMR (270 MHz, CDCl$_3$) δ7.68 (d, 1H, J=3.5 Hz) 6.87 (d, 1H, J=4 Hz) 6.39 (s, 1H) 5.11 (m, 1H) 3.87 (s, 3H) 2.21 (m, 4H) 2.01 (s, 3H) 1.69 (s, 3H) 1.62 (s, 3H) ppm. MC (CI-NH$_3$, +ions) m/e 282 (M+NH$_4$), 265 (M+H). Anal. calcd. for C$_{15}$H$_{20}$O$_2$S: C, 68.14; H, 7.62; S, 12.13 Found: C, 67.78; H, 7.67 ; S, 12.16

B. (E)-5-(2,6-Dimethyl-1,5-heptadienyl)-2-thiophenemethanol

To 239 mg (6.29 mmol) of lithium aluminum hydride under argon at 0° C. was added 30 mL of dry ether and 1.11 g (4.19 mmol) of Part A compound in 30 mL of dry ether was added dropwise over 10 min. After 20 min at 0° C. the reaction was quenched by the addition of 0.25 mL of H$_2$O, 0.25 mL of 15% NaOH solution and then with 0.75 mL of H$_2$O. The reaction was allowed to stir for 0.5 h, Na$_2$SO$_4$ was added and the slurry was allowed to stir for 1 h before filtering through a pad of celite washing copiously with ether. Evaporation provided 952 mg of a clear colorless oil which was combined with 167 mg from a previous reduction on 210 mg (0.794 mmol) of Part A compound. Flash chromatography was performed on 115 g of silica gel packed and loaded with 9:1 hexane/EtOAc and eluted with 7:1 hexane/EtOAc collecting 30 mL fractions. Fractions 29 to 57 were combined and evaporated to provide 1.06 g (92%) of title alcohol as a clear colorless oil.

TLC Silica gel (4:1 hexane/EtOAc) R$_f$=0.22. IR (CCl$_4$) 3333, 2966, 2924, 2856, 1446, 1376, 1209, 1009 cm$^{-1}$. $^1$H NMR (CDCl$_3$) δ6.88 (d, 1H, J=3.5 Hz) 6.76 (d, 1H, H=3.5 Hz) 6.34 (s, 1H) 5.12 (m, 1H) 4.77 (d, 2H, J=5 Hz) 2.17 (m, 4H) 1.97 (s, 3H) 1.69 (s, 3H) 1.62 (s, 3H) ppm. MS (CI-NH$_3$, +ions) m/e 237 (M+H), 219 (M+H-H$_2$O). Anal. calcd. for C$_{14}$H$_{20}$OS: C, 71.14; H, 8.52; S, 13.56 Found: C, 70.79; H, 8.68; S, 13.35

C. (E)-[[[5-(2,6-Dimethyl-1,5-heptadienyl)-2-thienyl]methoxy]methyl]phosphonic acid, bis(1-methylethyl) ester To a stirred solution of 1.06 g (4.48 mmol) of Part B alcohol in 20 mL of THF under argon at −78° C. was added 5.38 mL (5.38 mmol) of 1M lithium bis(trimethylsilyl)amide in THF over 5 min. The reaction was allowed to stir at −78° C. for 20 min when 1.47 g (4.48 mmol) of the Example 1 Part E(2) triflate in 30 mL of THF was added via cannula. The reaction was allowed to stir at −78° C. for 0.5 h and then warm to 0° C. and stir for 2 h when it was quenched by the addition of saturated NH$_4$Cl and partitioned between ether and water. The ether layer was washed with water, brine, dried over MgSO$_4$ and evaporated to provide 1.53 g of a yellow oil. Flash chromatography was performed on 160 g of silica gel packed and loaded with 3:1 hexane/EtOAc and eluted with 2:1 hexane/EtOAc collecting 30 mL fractions. Fractions 45 to 87 were combined and evaporated to provide 1.02 g (55%) of title compound as a yellow oil.

TLC Silica gel (1:1 hexane/EtOAc) R$_f$=0.21. IR (CCl$_4$) 2977, 2930, 1465, 1384, 1257, 1105, 989 cm$^{-1}$. $^1$H NMR (CDCl$_3$) δ6.90 (d, 1H, J=3.5 Hz) 6.76 (d, 1H, J=3.5 Hz) 6.34 (s, 1H) 5.12 (m, 1H) 4.79–4.72 (m, 2H) 4.75 (s, 2H) 3.70 (d, 2H, J=8.8 Hz) 2.17 (m, 4H) 1.96 (s, 3H) 1.69 (s, 3H) 1.62 (s, 3H) 1.32, 1.34 (two d, 12 H total, J=6 Hz) ppm. MS (CI-NH$_3$, +ions) m/e 432 (M+NH$_4$).

D. (E)-[[[5-(2,6-Dimethyl-1,5-heptadienyl)-2-thienyl]methoxy]methyl]phosphonic acid, mono(1-methylethyl) ester To a stirred solution of 983 mg (2.37 mmol) of Part C compound in 15 mL of 2-propanol under argon at RT was added 12 mL (12.0 mmol) of 1M KOH and the reaction was heated to 100° C. for 26 h. The 2-propanol solvent was evaporated and the aqueous residue was stirred in dichloromethane and acidified by the addition of 1M KHSO$_4$ solution. The organic layer was washed with water, brine, dried over MgSO$_4$ and 3 mL (17.2 mmol) of diisopropylethylamine was added. The solvent was evaporated to provide title compound as an oily yellow solid which was used directly in the following reaction.

TLC Silica gel (8:1:1 n-C$_3$H$_7$OH/con. NH$_3$/H$_2$O) R$_f$=0.57.

E. (E)-[[[5-(2,6-Dimethyl-1,5-heptadienyl)-2-thienyl]methoxy]methyl]fluorophosphinic acid, 1-methylethyl ester To a suspension of 883 mg (2.37 mmol) of Part D compound and 806 mg (2.84 mmol) of 2-fluoro-1-methylpyridium toluene-4-sulfonate in 10 mL of dichloromethane under argon at 0° C. was added 0.99 mL (5.69 mmol) of diisopropylethylamine dropwise. After stirring for 15 min at 0° C., the yellow solution was allowed to stir at RT overnight. The orange-yellow solution was diluted with ethyl acetate and washed with 1N HCl solution. All of the color went into the aqueous phase. The organic layer was washed with water, brine, dried over MgSO$_4$ and evaporated to provide 798 mg (90%) of title compound as a yellow oil.

TLC Silica gel (5:95 methanol/dichloromethane) R$_f$=0.88. $^1$H NMR (CDCl$_3$) δ6.92 (d, 1H, J=3.5 Hz) 6.77 (d, 1H, J=3.5 Hz) 6.35 (s, 1H) 5.12 (m, 1H) 4.95 (m, 1H) 4.78 (s, 2H) 3.87 (dd, 2H, J=8.8 Hz, 4 Hz) 2.17 (m, 4H) 1.97 (s, 3H) 1.69 (s, 3H) 1.62 (s, 3H) 1.39, 1.41 (two d, 12 H total, J=6 Hz) ppm.

F. (E)-[[[[5-(2,6-Dimethyl-1,5-heptadienyl)-2-thienyl]methoxy]methyl](1-methylethoxy)phosphinyl]methyl]phosphonic acid, dimethyl ester To a stirred solution of 0.50 mL (4.66 mmol) of dimethyl methylphosphonate in 10 mL of THF under argon at −78° C. was added 2.8 mL (4.45 mmol) of 1.6M n-BuLi in hexanes over 5 min to give a white suspension. The mixture was allowed to stir for 40 min at −78° C. when 794 mg (2.12 mmol) of Part E compound in 15 mL of THF was added dropwise over 5 min. The solution turned clear yellow after a few minutes and was allowed to stir at −78° C. for 1 h when it was quenched with saturated NH$_4$Cl and diluted with ethyl acetate. The aqueous layer was made acidic by the addition of 1M KHSO$_4$ solution. The organic layer was separated and washed with water and brine. The aqueous layer was reextracted with dichloromethane and the organic layer was washed with water and brine. The combined organic layers were dried over MgSO$_4$ and evaporated to provide 947 mg of a yellow oil. Flash chromatography was performed on 100 g of silica gel eluted with 2:98 methanol/dichloromethane collecting 30 mL fractions. Fractions 38 to 74 were combined and evaporated to provide 804 mg (79%) of title product as a clear colorless oil.

TLC Silica gel (5:95 methanol/dichloromethane) R$_f$=0.31. IR (CCl$_4$) 2957, 2926, 2855, 1462, 1254, 1035, 993 cm$^{-1}$. $^1$H NMR (CDCl$_3$) δ6.90 (d, 1H, J=3.5 Hz) 6.76 (d, 1H, J=3.5 Hz) 6.34 (s, 1H) 5.13 (m, 1H) 4.81–4.69 (m, 1H) 4.78 (d, 1H, J=13 Hz) 4.71 (d, 1H, J=13 Hz) 3.87–3.77 (m, 2H) 3.81, 3.77 (two d, 6H, total, J=11 Hz) 2.50 (m, 2H) 2.18 (m, 4H) 1.96 (s, 3H) 1.69 (s, 3H) 1.69 (s, 3H) 1.62 (s, 3H) 1.35, 1.32 (two d, 6 H total, J=6.45 Hz) ppm. MS (CI-NH$_3$, +ions) m/e 496 (M+NH$_4$) Anal. calcd. for C$_{21}$H$_{36}$O$_6$P$_2$S.0.46 H$_2$O: C, 51.81; H, 7.64; P, 12.72 Found: C, 51.81; H, 7.53; P, 12.63

EXAMPLE 8

(E)-[[[[[5-(2,6-Dimethyl-1,5-heptadienyl)-2-thienyl]methoxy]methyl]hydroxyphosphinyl]methyl]phosphonic acid, trisodium salt To a stirred solution of 500 mg (1.04 mmol) of Example 7 product in 7 mL of dichloromethane under argon at 0° C. was added 0.41 mL (3.12 mmol) of 2,4,6-collidine followed by 0.82 mL (6.24 mmol) of bromotrimethylsilane and the reaction was allowed to stir at RT for 24 h. The solvent was evaporated and pumped at high vacuum for 1 h. The remainder was dissolved in 6.3 mL (6.30 mmol) of 1M NaOH solution, stirred for 1 h, diluted with water and lyophilized to provide 846 mg of crude product. The material was purified by MPLC on a column of CHP-20P (2.5 cm diameter×21 cm height) eluted by the gradual addition of 50 mL of 70:30 CH$_3$CN/H$_2$O to a reservoir of 450 mL of water. Approximately 10 mL fractions were collected and the pH at fraction 15 was about pH =10. Fractions 41 to 46 were combined, the acetonitrile was evaporated at reduced pressure and the aqueous solution was lyophilized to provide 390 mg (79%) of title salt as an amorphous white lyophilate which was greater than 99% pure by HPLC.

TLC Silica gel (5:4:1 n-C$_3$H$_7$OH/con. NH$_3$/H$_2$O) R$_f$=0.35. IR (KBr) 3434, 29266, 2857, 1697, 1635, 1450, 1350, 1178, 1088, 1052 cm$^{-1}$. $^1$H NMR (D$_2$O) δ7.01 (d, 1H, J=3.5 Hz, H$_3$) 6.83 (d, 1H, J=3.5 Hz, H$_4$) 6.37 (s, 1H, H$_6$) 5.14 (m, 1H, H$_{10}$) 4.71 (s, 2H, H$_1$) 3.67 (d, 2H, J=5.9 Hz, H$_{15}$) 2.15 (m, 4H, H$_8$, H$_9$) 1.91 (s, 3H, H$_{14}$) 1.90 (t, 2H, J=8 Hz, H$_{16}$) 1.60 (s, 3H, H$_{12}$) 1.55 (s, 3H, H$_{13}$) ppm. MS (FAB, +ions) m/e 497 (M+Na), 475 (M+H). Anal. calcd. for C$_{16}$H$_{23}$Na$_3$O$_6$P$_2$S.1.25 H$_2$O: C, 38.67; H, 5.17; P, 12.47; S, 6.45 Found: C, 38.75; H, 5.37 ; P, 12.71; S, 6.45

EXAMPLE 9

(E)-[[[[[5-(2,6-Dimethyl-1,5-heptadienyl)-3-methyl-2-thienyl]methoxy]methyl](1-methylethoxy)phosphinyl]methyl]phosphonic acid, dimethyl ester SQ 35,167

A. 3-Methyl-2-thiophenemethanol

To 4.80 g (126.6 mmol) of lithium aluminum hydride (LAH) under argon at 0° C. was added 80 mL of THF and 12 g (84.4 mmol) of 3-methyl-2-thiophenecarboxylic acid in 30 mL of THF was added dropwise over 20 min. After addition, the reaction was allowed to warm to RT and stir for 2 h when it was quenched by the addition of 5 mL of H$_2$O, 5 mL of 15% NaOH solution, and finally with 15 mL of H$_2$O. After stirring for 0.5 h, Na$_2$SO$_4$ was added and the slurry was allowed to stir for 1 h before filtering through a pad of celite washing copiously with ether. Evaporation provided 9.37 g (86%) of title alcohol as a pale yellow oil.

TLC Silica gel (1:1 hexane/EtOAc) $R_f=0.69$ $^1$H NMR (CDCl$_3$) δ7.11 (d, 1H, J=5 Hz) 6.79 (d, 1H, J=5 Hz) 4.65 (d, 2H, J=4.7 Hz) 2.64 (broad s, 1H) 2.19 (s, 3H) ppm.

B. 5-Iodo-3-methyl-3-thiophenemethanol

The procedure of M. J. Klaus and B. A. Pawson (U.S. Pat. No. 4,256,878) was followed:

To a vigorously stirred solution of 4 g (31.2 mmol) of Part A alcohol in 50 mL of benzene was added 7.44 g (34.3 mmol) of mercury(II) oxide (yellow) and 7.92 g (31.2 mmol) of iodine alternately over 1.5 h. After addition was complete the mixture was stirred for an additional 1 h. The reaction was filtered to remove the orange mercury(II) iodide and the precipitate was washed copiously with ether. The organic layer was washed with saturated Na$_2$S$_2$O$_3$ solution, brine, dried over MgSO$_4$ and evaporated to provide 7.28 g (92%) of an orange-brown oil. Flash chromatography was performed on 700 g of silica gel packed and loaded with 7:1 hexane/EtOAc and eluted with 5:1 hexane/EtOAc collecting 100 mL fractions. Evaporation provided 6.59 g (83%) of title iodide as a pale orange-yellow oil.

TLC Silica gel (5:1 hexane/EtOAc) $R_f=0.20$ IR (CCl$_4$) 3322, 2920, 2871, 1424, 1381, 1356, 1167, 1000, 934, 831 cm$^{-1}$. $^1$H NMR (CDCl$_3$) δ6.96 (s, 1H) 4.68 (d, 2H, J=5.3 Hz) 2.18 (s, 3H) 1.95 (t, 1H, J=5.3 Hz) ppm. MS (CI-NH$_3$, +ions) m/e 254 (M), 237 (M+H-H$_2$O). Anal. calcd. for C$_6$H$_7$IOS C, 28.33 ; H, 2.79 ; I, 49.90; S, 12.61 Found: C, 28.63; H, 2.75; I, 49.48; S, 12.52

C. [[(5-Iodo-3-methyl-2-thienyl)methoxy]methyl]phosphonic acid, bis(1-methylethyl) ester To a stirred solution of 2 g (7.87 mmol) of Part B iodide in 30 mL of THF under argon at $-78°$ C. was added 8.7 mL (8.7 mmol) of 1M lithium bis(trimethylsilyl)amide in THF over 5 min. After addition, the reaction was allowed to stir for 20 min when 2.56 g (7.79 mmol) of the Example 1 Part E(2) triflate in 35 mL of THF was added via cannula. The reaction was allowed to stir at $-78°$ C. for 0.5 h and then warm to 0° C. and stir for 2 h when it was diluted with ether and quenched with saturated NH$_4$Cl solution. The reaction mixture was partitioned between ether and water and the organic layer was washed with water, brine, dried over MgSO$_4$ and evaporated to provide 3.45 g of a dark yellow oil. Flash chromatography was performed on 350 g of silica gel packed and loaded with 3:1 hexane/EtOAc and eluted with 2:1 hexane/EtOAc collecting 40 mL fractions. Fractions 60 to 137 were combined and evaporated to provide 2.47 g (73%) of title compound as a clear colorless oil. The oil solidified upon standing in the $-40°$ C. freezer. mp 39°-40° C.

TLC Silica gel (1:1 hexane/EtOAc) $R_f=0.25$. IR (KBr) 2979, 2932, 1634, 1386, 1241, 1104, 995 cm$^{-1}$. $^1$H NMR (CDCl$_3$) δ6.97 (s, 1H) 4.75 (m, 2H) 4.68 (s, 2H) 3.69 (d, 2H, J=8.8 Hz) 2.19 (s, 3H) 1.32, 1.34 (two d, 12H total, J=5.9 Hz) ppm. MS (CI-NH$_3$, +ions) m/e 450 (M+NH$_4$), 433 (M+H). Anal. calcd. for C$_3$H$_{22}$IO$_4$PS C, 36.12; H, 5.13; I, 29.36 P, 7.17; S, 7.42 Found: C, 36.43 ; H, 5.07; I, 29.50 P, 7.44; S, 7.20

D. (E)-[[[5-(2,6-Dimethyl-1,5-heptadienyl)-3-methyl-2-thienyl]methoxy]methyl]phosphonic acid, bis(1-methylethyl) ester To 30 mL of THF under argon at $-78°$ C. was added 43.7 mL (74.4 mmol) of 1.7M t-butyl-lithium in pentane to give a yellow solution. Example 1 Part B vinyl iodide (3.89 g, 15.5 mmol) in 25 mL of THF was added dropwise over 10 min and the reaction was allowed to stir at $-78°$ C. for 0.5 h and then warm to 0° C. and stir for 0.5 h. Zinc chloride (5.07 g, 37.2 mmol) (fuse-dried under vacuum three times) in 50 mL of THF was added via syringe to give a pale yellow solution which was allowed to stir at 0° C. for 1 h.

To a 250 mL RB in an argon filled glove bag was added 2.40 g (5.55 mmol) of Part C compound and 321 mg (0.277 mmol, 5 mol%) of tetrakis(triphenylphosphine)palladium. A volume of 15 mL of THF was added and the mixture was cooled to 0° C. The zinc intermediate prepared above was added via cannula and the reaction was allowed to warm to RT and stir for 2 h when it was diluted with ether and quenched with 1M HCl. The organic layer was washed with water, saturated NaHCO$_3$, brine, dried over MgSO$_4$ and evaporated to provide 3.45 g of an orange-yellow oil with solids present. Flash chromatography was performed on 300 g of silica gel packed and loaded with 4:1 hexane/EtOAc and eluted with 3:1 hexane/EtOAc collecting 50 mL fractions. Fractions 57 to 85 were combined and evaporated to provide 1.69 g (71%) of title compound as an orange-yellow oil.

TLC Silica gel (1:1 hexane/EtOAc) $R_f=0.26$. IR (CCl$_4$) 2977, 2927, 2876, 1451, 1375, 1257, 1106, 990 cm$^{-1}$. $^1$H NMR (CDCl$_3$) δ6.64 (s, 1H) 6.29 (s, 1H) 5.12 (m, 1H) 4.75 (m, 2H) 4.70 (s, 2H) 3.70 (d, 2H, J=8 Hz) 2.19 (s, 3H) 2.17 (m, 4H) 1.95 (s, 3H) 1.69 (s, 3H) 1.62 (s, 3H) 1.34, 1.32 (two d, 12 H total, J=6 Hz) ppm. Anal. calcd. for C$_{22}$H$_{37}$O$_4$PS.0.50 H$_2$O C, 60.39; H, 8.75; P, 7.08 Found: C, 60.40; H, 8.76; P, 7.24

E. (E)-[[[5-(2,6-Dimethyl-1,5-heptadienyl)-3-methyl-2-thienyl]methoxy]methyl]phosphonic acid, mono (1-methylethyl) ester To a stirred solution of 700 mg (1.63 mmol) of Part D compound in 20 mL of 2-propanol was added 8.3 mL (8.30 mmol) of 1 molar KOH solution and the reaction was heated to 100° C. under an argon atmosphere for 24 h. The 2-propanol solvent was evaporated and the aqueous solution was stirred in CH$_2$Cl$_2$ and acidified with 1M KHSO$_4$ solution. The organic layer was washed with water, brine, dried over MgSO$_4$ and 3 mL of N,N-diisopropylethylamine was added. The solvent was evaporated to provide the title N,N-diisopropylethylamine salt as an oily yellow solid which was used directly in the next step.

TLC Silica gel (8:1:1 n-C$_3$H$_7$OH/con NH$_3$/H$_2$O) $R_f=0.51$.

F. (E)-[[[5-(2,6-Dimethyl-1,5-heptadienyl)-3-methyl-2-thienyl]methoxy]methyl]fluorophosphinic acid, 1-methylethyl ester To a suspension of 554 mg (1.96 mmol) of Part E salt and 630 mg (1.63 mmol) of 2-fluoro-1-methylpyridinium toluene-4-sulfonate in 20 mL of CH$_2$Cl$_2$ under argon at 0° C. was added 0.39 mL (2.28 mmol) of N,N-diisopropylethylamine dropwise. The reaction was allowed to stir at 0° C. for 15 min and then warm to RT and stir overnight. The orange-yellow solution was diluted with ethyl acetate and washed with 1M HCl solution. All of the color went into the aqueous phase. The organic layer was washed with water, brine, dried over MgSO$_4$ and evaporated to provide 607 mg (96%) of title compound as a pale yellow oil which was used directly as the crude in the following reaction.

TLC Silica gel (5:95MeOH/CH$_2$Cl$_2$) R$_f$=0.67. $^1$H NMR (CDCl$_3$) δ6.66 (s, 1H) 6.29 (s, 2H) 5.12 (m, 1H) 4.95 (m, 1H) 3.86 (dd, 2H, J=4 Hz, J=8 Hz) 2.19 (s, 3H) 1.95 (s, 3H) 1.69 (s, 3H) 1.62 (s, 3H) 1.41, 1.39 (two d, 6H total, J=4 Hz) ppm.

G.
(E)-[[[[[5-(2,6-Dimethyl-1,5-heptadienyl)-3-methyl-2-thienyl]methoxy]methyl](1-methylethoxy)phosphinyl]methyl]phosphinic acid, dimethyl ester To a stirred solution of 0.37 mL (3.44 mmol) of dimethyl methylphosphonate in 2 mL of THF under argon at −78° C. was added 2 mL (3.28 mmol) of 1.6M n-butyllithium in hexanes over 5 min to give a white suspension. The mixture was allowed to stir at −78° C. for 40 min when 607 mg (1.56 mmol) of Part F compound in 5 mL of THF was added over 5 min resulting in a clear yellow solution. The reaction was allowed to stir for 1 h at −78° C. when it was diluted with ether and quenched by the addition of saturated NH$_4$Cl solution. The aqueous layer was made acidic by the addition of 1M KHSO$_4$ solution and the organic layer was separated and washed with water and brine. The aqueous layer was reextracted with dichloromethane and the dichloromethane layer was washed with water and brine. The combined organic layers were dried over MgSO$_4$ and evaporated to provide 746 mg of a yellow oil. Flash chromatography was performed on 75 g of silica gel packed, loaded and eluted with 2:98 MeOH/CH$_2$Cl$_2$ collecting 50 mL fractions. Fractions 58 to 71 were combined and evaporated to provide 471 mg (61%) of title produce as a pale yellow oil.

TLC Silica gel (5:95MeOH/CH$_2$Cl) R$_f$=0.26. IR (CCl$_4$) 2958, 2924, 1670, 1450, 1375, 1250, 1034, 993 cm$^{-1}$. $^1$H NMR (CDCl$_3$) δ6.65 (s, 1H) 6.28 (s, 1H) 5.11 (m, 1H) 4.76 (m, 1H) 4.72 (d, 1H, J=12.9 Hz) 4.66 (d, 1H, J=12.9 Hz) 3.89 –3.76 (m, 2H) 3.81, 3.78 (two d, 6H total, J=11 Hz) 2.49 (m, 2H) 2.19 (s, 3H) 2.16 (m, 4H) 1.94 (d, 3H, J=1 Hz) 1.69 (s, 3H) 1.62 (s, 3H) 1.36, 1.32 (two d, 6H total, J=6.4 Hz) ppm. Anal. calcd. for C$_{22}$H$_{38}$O$_6$P$_2$S.0.50 H$_2$O C, 52.68; H, 7.84; P, 12.35; S, 6.39 Found: C, 52.66; H, 7.70; P, 12.45; S, 6.18

EXAMPLE 10
(E)-[[[[[5-(2,6-Dimethyl-1,5-heptadienyl)-3-methyl-2thienyl]methoxy]methyl]hydroxyphosphinyl]methyl]phosphonic acid, trisodium salt To a stirred solution of 450 mg (0.914 mmol) of Example 9 compound in 7 mL of dichloromethane under argon at 0° C. was added 0.36 mL (2.74 mmol) of 2,4,6-collidine followed by 0.72 mL (5.48 mmol) of bromotrimethylsilane and the reaction was allowed to warm to RT and stir for 24 h. The solvent was evaporated and pumped at high vacuum for 1 h. The remainder was dissolved in 5.5 mL (5.50 mmol) of 1M NaOH solution, stirred for 1 h, diluted with H$_2$O and lyophilized to provide 788 mg of crude lyophilate. The crude material was purified by MPLC on a column of CHP-20P (2.5 cm diameter×23 cm height) eluted with water fractions (1 to 16) followed by a gradient created by the gradual addition of 500 mL of a 70:30 CH$_3$CN/H$_2$O to a reservoir of 450 mL of water. Approximately 10 mL fractions were collected and the pH at fraction 16 was about pH=10. Fractions 49 to 53 were combined, the acetonitrile was evaporated at reduced pressure and the aqueous solution was lyophilized to provide 258 mg (58%) of title salt as an amorphous white lyophilate.

TLC Silica gel (5:4:1 n-C$_3$H$_7$OH/con NH$_3$/H$_2$O) R$_f$=0.42. IR (KBr) 3439, 2967, 2924, 2859, 1637, 1447, 1375, 1177, 1088, 1053, 974 cm$^{-1}$. $^1$H NMR (D$_2$O) δ6.76 (s, 1H) 6.33 (s, 1H) 5.16 (m, 1H) 4.68 (s, 2H) 3.69 (d, 2H, J=6.45 Hz) 2.16 (m, 7H) 1.94 (t, 2H, J=18 Hz) 1.91 (s, 3H) 1.63 (s, 3H) 1.57 (s, 3H) ppm. MS (FAB, +ions) m/e 511 (M+Na), 489 (M+H). Anal. calcd. for C$_{17}$H$_{25}$Na$_3$O$_6$P$_2$S.1.50 H$_2$O C, 39.62; H, 5.48; P, 12.02; S, 6.22 Found: C, 39.76; H, 5.30; P, 12.23; S, 6.62

EXAMPLE 11
(E)-[[[[[3-(2,6-Dimethyl-1,5-heptadienyl)phenyl]methoxy]methyl]hydroxyphosphinyl]methyl]phosphonic acid, trisodium salt

A. (E)-3-(2,6-Dimethyl-1,5-heptadienyl)benzoic acid, methyl ester

A(1). Methyl 3-iodobenzoate

To a stirred solution of 25 g (100.8 mmol) of 3-iodobenzoic acid in 250 mL of methanol under argon was added 1.2 mL (23.2 mmol) of concentrated H$_2$SO$_4$ and the mixture was heated to reflux for 24 h. The solution was concentrated to 150 mL, gravity filtered to remove any insoluble material, scratched with a glass rod, and allowed to cool slowly. After cooling to RT the flask was allowed to stand in the refrigerator for a few days. The solid was collected and washed with ice cold methanol and dried under high vacuum at RT for 2 days to provide 25.7 g (97%) of a light violet colored solid. mp 40°–41° C.

TLC Silica gel (9:1 hexane/ethyl acetate) R$_f$=0.33 $^1$H NMR (270 MHz, CDCl$_3$) δ8.37 (t, 1H, J=1.76 Hz) 7.99 (m, 1H) 7.88 (m, 1H) 7.17 (t, 1H, J=8 Hz) 3.91 (s, 3H) ppm. $^{13}$C NMR (CDCl$_3$) δ165.5, 141.7, 138.4, 132.0, 130.0, 128.7, 93.7, 52.3 ppm.

A(2). (E)-3-(2,6-Dimethyl-1,5-heptadienyl)-benzoic acid, methyl ester

To 12 mL of THF under argon at −78° C. was added 7.5 mL (12.8 mmol) of 1.7M t-butyllithium in pentane to give a yellow solution to which 1.34 g (5.35 mmol) of Example 1 Part B vinyl iodide in 10 mL 5 of THF was added dropwise over 10 min. After addition, the reaction was allowed to stir at −78° C. for 0.5 h and then warm to 0° C. for 0.5 h. Zinc chloride (873 mg, 6.41 mmol, fuse-dried under vacuum three times) in 10 mL of THF was added via cannula to give a pale yellow solution which was allowed to stir at 0° C. for 1 h.

A 100 mL RB flask was charged with 308 mg (0.266 mmol, 5 mol %) of tetrakis(triphenylphosphine)palladium (0) and 1.0 g (3.82 mmol) of methyl 3-iodobenzoate in an argon filled glove bag. A volume of 7 mL of THF was added and the suspension was cooled to 0° C. when the zinc intermediate prepared above was added via cannula. The mixture was allowed to warm to RT and stir for 1 h when it was diluted with ether and quenched by the addition of 1N HCl solution. The organic layer was washed with water, saturated NaHCO$_3$, brine, dried over MgSO$_4$ and evaporated to provide 1.35 g of an orange-yellow oily solid. Flash chromatography was performed on 140 g of silica gel packed with 5:1 hexane/toluene and eluted with 3:1 hexane/toluene collecting 50 mL fractions. Fractions 58 to 87 were combined and evaporated to provide 715 mg (72%) of title compound as a clear, colorless oil.

TLC Silica gel (9:1 hexane/EtOAc) $R_f=0.38$ IR (CCl$_4$) 2969, 2914, 2855, 1726, 1437, 1290, 1209, 1107, 1084, 731 cm$^{-1}$ $^1$H NMR (CDCl$_3$) $\delta$7.91 (s, 1H) 7.85 (td, 1H, J=7 Hz and 2 Hz) 7.38 (m, 2H) 6.28 (s, 1H) 5.16 (m, 1H) 3.91 (s, 3H) 2.21 (m, 4H) 1.86 (s, 3H) 1.71 (s, 3H) 1.64 (s, 3H) ppm. MS (CI-NH$_3$, +ions) m/e 276 (M+NH$_4$), 259 (M+H). Anal. calcd. for C$_{17}$H$_{22}$O$_2$: C, 79.03 ; H, 8.58 Found: C, 79.23 ; H, 8.56

B.
(E)-3-(2,6-Dimethyl-1,5-heptadienyl)benzenemethanol

To 154 mg (4.06 mmol) of lithium aluminum hydride under argon at 0° C. was added 10 mL of dry ether, and 700 mg (2.71 mmol) of Part A compound in 15 mL of dry ether was added dropwise over 5 min. The reaction was allowed to stir at 0° C. for 0.5 h when it was quenched by the addition of 0.16 mL of H$_2$O 0.16 mL of 15% NaOH and then with 0.49 mL of H$_2$O. After stirring for 0.5 h, Na$_2$SO$_4$ was added and the slurry was allowed to stir for 1 h before filtering through a pad of celite washing copiously with ether. Evaporation provided 612 mg of a crude oil. Flash chromatography was performed on 70 g of silica gel packed with 15:1 hexane/EtOAc and eluted with 9:1 hexane/EtOAc collecting 50 mL fractions. Fractions 28 to 41 were combined and evaporated to provide 568 mg (91%) of title compound as a clear, colorless oil.

TLC Silica gel (9:1 dichloromethane/EtOAc) $R_f=0.56$ IR (CCl$_4$) 3615, 2969, 2914, 2878, 2857, 1603, 1483, 1443, 1377, 1167, 1018, 731 cm$^{-1}$ $^1$H NMR (CDCl$_3$) $\delta$7.28 (t, 1H, J=7 Hz) 7.18 (m, 3H) 6.26 (s, 1H 5.17 (m, 1H) 4.64 (d, 2H, J=5 Hz) 2.19 (m, 4H) 1.85 (s, 3H) 1.70 (s, 3H) 1.64 (s, 3H) ppm. MS (CI-NH$_3$, +ions) m/e 248 (M+NH$_4$), 231 (M+H).

C.
(E)-[[[3-(2,6-Dimethyl-1,5-heptadienyl)-phenyl]methoxy]methyl]phosphonic acid, bis (1-methylethyl) ester To a stirred solution of 563 mg (2.44 mmol) of Part B compound in 7 mL of THF under argon at −78° C. was added 1.6 mL (2.57 mmol) of 1.6M n-butyllithium in hexanes over 5 min. The pale yellow solution was allowed to stir at −78° C. for 40 min when 793 mg (2.41 mmol) of the Example 1 Part E(2) triflate in 10 mL of THF was added via cannula. The mixture was allowed to stir at −78° C. for 0.5 h and then warm to 0° C. and stir for 1.5 h when it was diluted with ether and quenched by the addition of saturated NH$_4$Cl. The ether layer was washed with water, brine, dried over MgSO$_4$ and evaporated to provide 930 mg of a pale yellow oil. Flash chromatography was performed on 100 g of silica gel packed with 15:1 dichloromethane/EtOAc and eluted with 12:1 dichloromethane/EtOAc collecting 50 mL fractions. Fractions 34 to 59 were combined and evaporated to provide 712 mg (72%) of title compound as a colorless oil.

TLC Silica gel (9:1 dichloromethane/EtOAc) $R_f=0.20$ IR (CCl$_4$) 2978, 2932, 2879, 2857, 1385, 1257, 1107, 1008, 991, 816 cm$^{-1}$ $^1$H NMR (270MHz, CDCl$_3$) $\delta$7.27 (d, 1H, J=7 Hz) 7.16 (m, 3H, H$_2$, H$_4$) 6.25 (s, 1H) 5.17 (m, 1H) 4.76 (m, 2H) 4.63 (s, 2H) 3.71 (d, 2H, J=8 Hz) 2.19 (m, 4H) 1.85 (s, 3H) 1.70 (s, 3H) 1.33 (t, 12H, J=5.6 Hz) ppm. MS (CI-NH$_3$, +ions) m/e 426 (M+NH$_4$), 409 (M+H).

D.
(E)-[[[3-(2,6-Dimethyl-1,5-heptadienyl)phenyl]methoxy]methyl]phosphonic acid, mono (1-methylethyl) ester To a stirred solution of 709 mg (1.73 mmol) of Part C compound in 10 mL of 2-propanol under argon was added 9 mL (9.00 mmol) of 1.0M KOH and the solution was heated to 100° C. for 18 h. The 2-propanol solvent was evaporated and the aqueous residue was stirred in dichloromethane and acidified with 10% HCl solution. The organic layer was washed with water, brine, dried over MgSO$_4$ and evaporated to provide 605 mg (95%) of title compound as a clear colorless oil.

TLC Silica gel (8:1:1 n-C$_3$H$_7$OH/con NH$_3$/H$_2$O) $R_f=0.56$ (E)-[[[[[3-(2,6-Dimethyl-1,5-heptadienyl)phenyl]methoxy]methyl](1-methylethoxy)phosphinyl]methyl]phosphonic acid, dimethyl ester To a stirred solution of 605 mg (1.65 mmol) of Part D compound in 7 mL of dichloromethane under argon at RT was added 0.63 mL (3.30 mmol) of N,N-diethyltrimethylsilylamine and the reaction was allowed to stir at RT for 1.5 h. The solvent was evaporated and the residue was dissolved in benzene, evaporated and pumped at high vacuum. The remainder was dissolved in 10 mL of dichloromethane containing 3 drops of DMF under nitrogen at 0° C. and 1.65 mL (3.30 mmol) of 2M oxalyl chloride in dichloromethane was added dropwise over 10 min. with much gas evolution. After 45 min. at 0° C. the reaction was allowed to stir at RT for 45 min. The solvent was evaporated and the residue was dissolved in benzene, evaporated and then pumped at high vacuum for 1 h.

To a solution of 0.39 mL (3.63 mmol) of dimethyl methylphosphonate in 7 mL of THF under argon at −78° C. was added 2.2 mL (3.46 mmol) of 1.6M n-butyllithium in hexanes over 10 min to give a white suspension. After 40 min. at −78° C., the acid chloride prepared above was added in 10 mL of THF over 10 min. and the reaction was allowed to stir at −78° C. for 1 h when it was quenched with saturated NH$_4$Cl and diluted with ether. The aqueous layer was made acidic with 10% HCl solution and the ether layer was separated and washed with brine. The aqueous layer was re-extracted with dichloromethane and the dichloromethane layer was washed with brine. The combined organic layers were dried over MgSO$_4$ and evaporated to provide 944 mg of a yellow oil. Flash chromatography was performed on 100 g of silica gel packed and loaded and eluted with 2:98 methanol/dichloromethane collecting 50 mL fractions. Fractions 38 to 57 were combined and evaporated to provide 548 mg (70%) of title product as a clear colorless oil.

TLC Silica gel (5:95 methanol/dichloromethane) $R_f=0.25$ IR (CCl$_4$) 2978, 2953, 2930, 2854, 1450, 1385, 1256, 1231, 1178, 1167, 1103, 1063, 1036, 993, 841, 816, 731 cm$^{-1}$ $^1$H NMR (CDCl$_3$) $\delta$7.27 (t, 1H, J=7 Hz) 7.16 (m, 3H, H$_2$, H$_4$) 6.25 (s, 1H) 5.16 (m, 1H) 4.77 (m, 1H) 4.66 (d, 1H, J=12 Hz) 4.58 (d, 1H, J=12 Hz) 3.88–3.75 (m, 2H) 3.79, 3.78 (two d, 6H total, J=11 Hz) 2.50 (m, 2H) 2.19 (m, 4H) 1.85 (s, 3H) 1.70 (s, 3H) 1.64 (s, 3H) 1.36, 1.3 1 (two d, 6H total, J=6 Hz) ppm. MS (CI-NH$_3$, +ions) m/e 490 (M+NH$_4$), 473 (M+H)

EXAMPLE 12

(E)-[[[[[3-(2,6-Dimethyl-1,5-heptadienyl)phenyl]methoxy]methyl]hydroxyphosphinyl]methyl]phosphonic acid, trisodium salt To a stirred solution of 541 mg (1.14 mmol) of Example 11 product in 7 mL of dichloromethane under argon at RT was added 0.45 mL (3.42 mmol) of 2,4,6-collidine followed by 0.90 mL (6.84 mmol) of bromotrimethylsilane and the reaction was allowed to stir at RT for 16 h. The solvent was evaporated and pumped at high vacuum for 1 h. The remainder was dissolved in 7.0 mL (7.00 mmol) of 1M NaOH solution, stirred for 1 h, diluted with water and lyophilized. The crude material was purified by MPLC on a column of CHP20P gel (2.5 cm diameter×21 cm height) eluted with water (fractions 1 to 12) followed by a gradient created by the gradual addition of 500 mL of acetonitrile to a reservoir of 450 mL of water. Approximately 12 mL fractions were collected and the pH at fraction 12 was about pH=10. Fractions 26 to 34 were combined, the acetonitrile was removed at reduced pressure and the aqueous solution was lyophilized to provide 488 mg (91%) of title product as an amorphous white lyophilate.

TLC Silica gel (5:4:1 n-$C_3H_7OH$/con. $NH_3/H_2O$) $R_f$=0.32 IR (KBr) 3428, 3416, 2924, 1647, 1445, 1377, 1178, 1150, 1094, 1057, 974, 874, 791, 704 $cm^{-1}$ $^1H$ NMR ($D_2O$) δ7.35 (t, 1H, J=7.5 Hz) 7.26 (m, 3H) 6.29 (s, 1H) 5.20 (m, 1H) 4.60 (s, 2H) 3.69 (d, 2H, J=6.2 Hz) 2.18 (m, 4H) 1.94 (t, 2H, J=18 Hz) 1.82 (s, 3H) 1.65 (s, 3H) 1.59 (s, 3H) ppm. MS (FAB, +ions) m/e 469 (M+H), 447 (M+2H-Na). Anal. calcd. for $C_{18}H_{25}Na_3O_6P_2 \cdot 1.5 H_2O$ C, 43.65; H, 5.70; P, 12.51 Found: C, 43.62; H, 5.61; P, 12.63

What is claimed is:

1. A compound having the structure

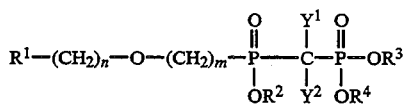

wherein m is 0, 1, 2 or 3; n is 1, 2, 3, 4 or 5; $Y^1$ and $Y^2$ are H or halogen;

$R^2$, $R^3$ and $R^4$ may be the same or different and are independently H, metal ion, $C_1$ to $C_8$ alkyl, $C_3$ to alkenyl, or prodrug ester; and $R^1$ is a substituted or unsubstituted heteroaryl group linked directly to $(CH_2)_n$ or indirectly to $(CH_2)_n$ through an alkylene, alkenylene or alkynylene linking group, and including a stereoisomer thereof or a pharmaceutically acceptable salt thereof, wherein heteroaryl is furanyl or thiofuranyl, and heteroaryl is optionally substituted with 1 to 3 groups selected from alkyl, alkoxy, alkenyl, alkenyloxy, alkynyl, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino.

2. The compound as defined in claim 1 wherein $R^1$ is $R^5$—Q—Y— or $R^5$—Y—Q wherein Y represents a substituted heteroaryl group;

Q is an alkylene linking group, an alkylene linking group or an alkynylene linking group or a single bond;

$R^5$ is hydrogen, alkyl, alkenyl or alkynyl, or a pharmaceutically acceptable salt thereof.

3. The compound as defined in claim 1 wherein $R^1$ is substituted furanyl, substituted thiofuranyl, substituted pyridinyl or substituted pyrrolyl.

4. The compound as defined in claim 2 wherein Q is

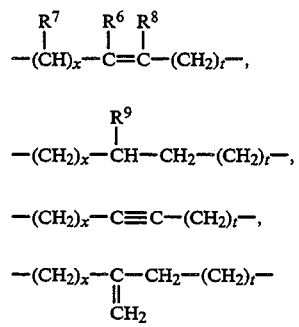

or a single bond, wherein t is 0, 1, 2 or 3, and x is 0, 1, 2 or 3; $R^6$ is H, lower alkyl, halo or haloalkyl; $R^7$ is H, halogen, lower alkyl or alkylthio; $R^8$ is H, halogen, trimethylsilyl or lower alkyl; and $R^9$ is H or lower alkyl; $R^5$ is H,

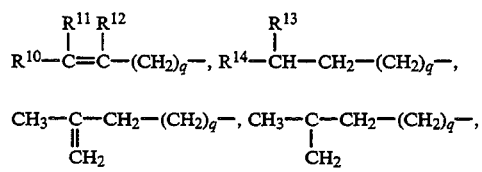

$CH_3(CH_2)_q$—, or $R^{16}$—C≡C—$(CH_2)_q$— or where $R^{16}$ is H or lower alkyl; q is 0, 1, 2, 3, 4 or 5; $R^{10}$ and $R^{11}$ are the same or different and are independently H, lower alkyl, haloalkyl, halogen or lower alkenyl or $R^{10}$ and $R^{11}$ can be taken together to form $(CH_2)_s$ where s is an integer from 2 to 7; $R^{12}$ is H, lower alkyl, halogen or lower alkenyl; and $R^{13}$ and $R^{14}$ are the same or different and are independently lower alkyl.

5. The compound as defined in claim 4 wherein $R^1$ is

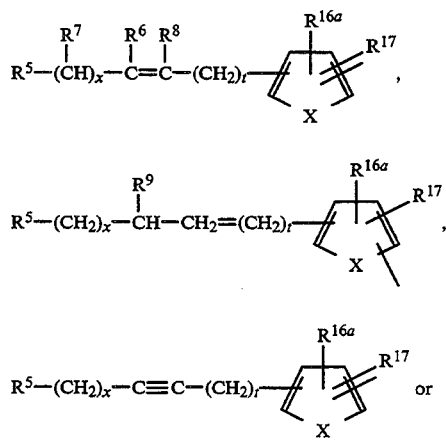

-continued

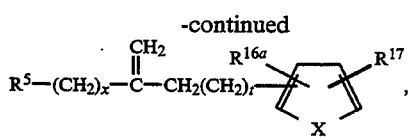

wherein X is O or S and $R^{16a}$ and $R^{17}$ are the same or different and are H, alkyl containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino.

6. The compound as defined in claim 2 wherein $R^1$ is

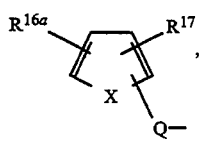

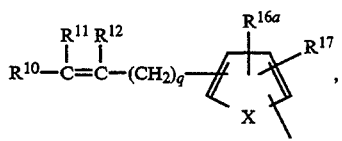

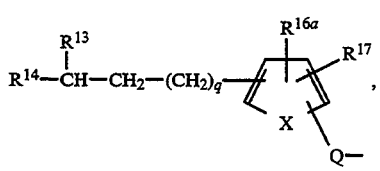

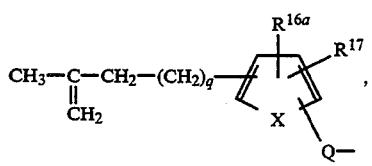

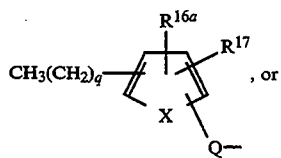

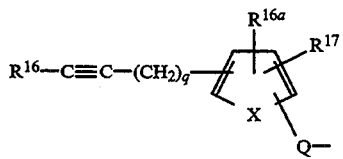

wherein X is O or S;
q is 0 to 5;
$R^{10}$ and $R^{11}$ are independently hydrogen, lower alkyl, halogen, lower alkenyl or haloalkyl, or $R^{10}$ and $R^{11}$ can be taken together to form $(CH_2)_s$, where s is 2 to 7; $R^{12}$ is hydrogen, lower alkyl, halogen or lower alkenyl; $R^{13}$ and $R^{14}$ are independently lower alkyl; $R^{16a}$ and $R^{17}$ are the same or different and are H, alkyl, containing 1 to 40 carbons, alkoxy containing 1 to 40 carbons, alkenyl containing 2 to 40 carbons, alkenyloxy containing 2 to 40 carbons, alkynyl containing 2 to 40 carbons, alkynyloxy, aryloxy, hydroxy, halogen, nitro, amino, thiol, alkylthio, arylthio, arylsulfinyl, alkylsulfinyl, arylsulfonyl, alkylsulfonyl, carboxy, alkoxycarbonyl, alkylcarbonyloxy, arylcarbonyloxy, aminocarbonyl, arylcarbonylamino or alkylcarbonylamino.

7. The compound as defined in claim 1 wherein $R^1$ is substituted with at least one substituent which is alkyl or alkenyl.

8. The compound as defined in claim 7 wherein $R^1$ includes a second substituent which is alkyl.

9. The compound as defined in claim 2 wherein $R^5$—Q—Y— is

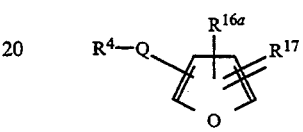

wherein $R^5$ is

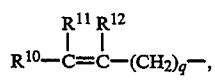

$R^{16a}$ is H or alkyl and $R^{17}$ is H.

10. The compound as defined in claim 2 wherein $R^5$—Q—Y is

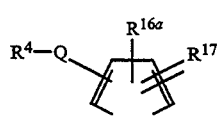

wherein $R^5$ is

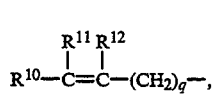

$R^{16a}$ is H or alkyl and $R^{17}$ is H.

11. The compound as defined in claim 2 wherein $Y^1$ and $Y^2$ are each F.

12. The compound as defined in claim 2 wherein $Y^1$ and $Y^2$ are each H.

13. The compound as defined in claim 2 wherein m is 1 or 2 and n is 1 or 2.

14. The compound as defined in claim 2 wherein n is 1, m is 1, $Y^1$ and $Y^2$ are H.

15. The compound as defined in claim 2 wherein one or more of $R^2$, $R^3$ and $R^4$ are an alkali metal salt or alkaline earth metal salt.

16. The compound as defined in claim 2 wherein $R^2$, $R^3$ and $R^4$ are each H.

17. The compound as defined in claim 2 where one or more of $R^2$, $R^3$ and $R^4$ are lower alkyl or lower alkenyl.

18. A hypocholesterolemic or hypolipemic composition comprising a compound as defined in claim 1 and a pharmaceutically acceptable carrier therefor.

* * * * *

UNITED STATES PATENT AND TRADEMARK OFFICE
CERTIFICATE OF CORRECTION

PATENT NO. : 5,374,628
DATED : December 20, 1994
INVENTOR(S) : Scott A. Biller

It is certified that error appears in the above-identified patent and that said Letters Patent is hereby corrected as shown below:

Column 55:

In Claim 1, line 47, after "$C_3$ to" please add --$C_{12}$--.

Signed and Sealed this

Twenty-second Day of August, 1995

BRUCE LEHMAN

*Attest:*

*Attesting Officer*     Commissioner of Patents and Trademarks